US012186428B2

(12) United States Patent
Egan et al.

(10) Patent No.: US 12,186,428 B2
(45) Date of Patent: *Jan. 7, 2025

(54) COMBINATION TAXOID NANOEMULSION WITH IMMUNOTHERAPY IN CANCER

(71) Applicants: TargaGenix, Inc., Stony Brook, NY (US); The Research Foundation for the State University New York, Albany, NY (US); Northeastern University, Boston, MA (US)

(72) Inventors: James E. Egan, Stony Brook, NY (US); Mansoor M. Amiji, Attleboro, MA (US); Iwao Ojima, Port Jefferson, NY (US)

(73) Assignees: TargaGenix, Inc., Stony Brook, NY (US); The Research Foundation for the State University of New York, Albany, NY (US); Northeastern University, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/986,430

(22) Filed: Nov. 14, 2022

(65) Prior Publication Data

US 2023/0082272 A1 Mar. 16, 2023

Related U.S. Application Data

(62) Division of application No. 16/225,629, filed on Dec. 19, 2018, now Pat. No. 11,497,713.

(60) Provisional application No. 62/608,015, filed on Dec. 20, 2017.

(51) Int. Cl.
*A61K 9/107* (2006.01)
*A61K 31/337* (2006.01)
*A61K 39/00* (2006.01)
*A61K 39/395* (2006.01)
*A61K 47/44* (2017.01)
*A61K 47/54* (2017.01)
*A61P 35/00* (2006.01)
*C07K 16/28* (2006.01)

(52) U.S. Cl.
CPC .......... *A61K 9/1075* (2013.01); *A61K 31/337* (2013.01); *A61K 39/39558* (2013.01); *A61K 47/44* (2013.01); *A61K 47/542* (2017.08); *A61P 35/00* (2018.01); *C07K 16/2827* (2013.01); *A61K 2039/505* (2013.01)

(58) Field of Classification Search
CPC ............... A61K 9/1075; A61K 31/337; A61K 39/39558; A61K 47/44; A61K 47/542; A61K 2039/505; A61P 35/00; A61P 35/02; C07K 16/2827

See application file for complete search history.

(56) References Cited

U.S. PATENT DOCUMENTS

| 7,820,839 | B2* | 10/2010 | Ojima | A61P 35/00 |
| | | | | 549/511 |
| 10,206,875 | B2* | 2/2019 | Egan | A61K 9/51 |
| 11,497,713 | B2* | 11/2022 | Egan | A61K 47/44 |
| 2007/0148194 | A1* | 6/2007 | Amiji | A61K 9/0095 |
| | | | | 424/400 |

OTHER PUBLICATIONS

Ahmad, et al., Cancer Letters 2017, 406:71 (Year: 2017).*
BMS, Clinical Trial No. NCT00730639, Aug. 7, 2008; Available online: https://www.clinicaltrials.gov/study/NCT00730639?cond=NCT00730639&rank=1&tab=history&a=1 (Year: 2008).*
Bellet, et al., Journal of Clinical Oncology 2004, 22:1457 (Year: 2004).*
Celgene, Clinical Trial No. NCT02309177, Dec. 4, 2014; Available online: https://www.clinicaltrials.gov/study/NCT02309177?cond=NCT02309177&rank=1&tab=history&a=1 (Year: 2014).*
Theradex, US clinical trial: NCT00024375; Jun. 23, 2005; URL: https://www.clinicaltrials.gov/study/NCT00024375?cond=NCT00024375&rank=1&tab=history&a=1 (Year: 2005).*
Siegel RL, Miller KD, Jemal A. Cancer statistics, 2015. CA Cancer J Clin 2015;65: 5-29.
Semenas J, Allegrucci C, Boorjian SA, Mongan NP, Persson JL. Overcoming drug resistance and treating advanced prostate cancer. Curr Drug Targets 2012;13: 1308-23.
Vredenburg MR, Ojima I, Veith J, Pera P, Kee K, Cabral F, Sharma A, Kanter P, Greco WR, Bernacki RJ. Effects of orally active taxanes on P-glycoprotein modulation and colon and breast carcinoma drug resistance. Journal of the National Cancer Institute 2001;93: 1234-45.
Von Hoff DD, Ervin T, Arena FP, Chiorean EG, Infante J, Moore M, Seay T, Tjulandin SA, Ma WW, Saleh MN, Harris M, Reni M, et al. Increased survival in pancreatic cancer with nab-paclitaxel plus gemcitabine. N Engl J Med 2013;369: 1691-703.
Conroy T, Desseigne F, Ychou M, Bouche O, Guimbaud R, Becouam Y, Adenis A, Raoul JL, Gourgou-Bourgade S, de la Fouchardiere C, Bennouna J, Bachet JB, et al. Folfirinox versus gemcitabine for metastatic pancreatic cancer. N Engl J Med 2011;364: 1817-25.
Hutchinson L, Kirk R. High drug attrition rates—where are we going wrong? Nature reviews Clinical oncology 2011;8: 189-90.
Zhu L, Gibson P, Currle DS, Tong Y, Richardson RJ, Bayazitov IT, Poppleton H, Zakharenko S, Ellison DW, Gilbertson RJ. Prominin 1 marks intestinal stem cells that are susceptible to neoplastic transformation. Nature 2009;457: 603-7.

(Continued)

*Primary Examiner* — Julie Wu
*Assistant Examiner* — Sydney Van Druff
(74) *Attorney, Agent, or Firm* — Kohn & Associates PLLC; Kenneth I. Kohn; Laura S. Dellal

(57) ABSTRACT

A composition of an omega-3 polyunsaturated fatty acid (PUFA)-taxoid conjugate formulated in an oil-in-water nanoemulsion (NE) drug delivery system in combination with an immune-oncology (IO) agent to enhance therapeutic efficacy in refractory cancers, such as PDAC. A method of treating cancer, by administering an effective amount of a pharmaceutical composition including an omega03 PUFA-taxoid conjugate in combination with an IO agent encapsulated in an NE drug delivery system to a subject in need of treatment, and treating cancer.

16 Claims, 21 Drawing Sheets

(56) References Cited

OTHER PUBLICATIONS

Ojima I, Chen J, Sun L, Borella CP, Wang T, Miller ML, Lin S, Geng X, Kuznetsova L, Qu C, Gallager D, Zhao X, et al. Design, synthesis, and biological evaluation of new-generation taxoids. J Med Chem 2008;51: 3203-21.
Botchkina GI, Zuniga ES, Das M, Wang Y, Wang H, Zhu S, Savitt AG, Rowehl RA, Leyfman Y, Ju J, Shroyer K, Ojima I. New-generation taxoid SB-T-1214 inhibits stem cell-related gene expression in 3D cancer spheroids induced by purified colon tumor-initiating cells. Molecular cancer 2010;9: 192.
Das M, Zuniga E, Ojima I. Novel Taxoid-Based Tumor-Targeting Drug Conjugates. Chim Oggi 2009;27: 54-6.
Sauer LA, Dauchy RT. The effect of omega-6 and omega-3 fatty acids on 3H-thymidine incorporation in hepatoma 7288CTC perfused in situ. British journal of cancer 1992;66: 297-303.
Harries M, O'Donnell A, Scurr M, Reade S, Cole C, Judson I, Greystoke A, Twelves C, Kaye S. Phase I/II study of DHA-paclitaxel in combination with carboplatin in patients with advanced malignant solid tumours. British journal of cancer 2004;91: 1651-5.
Hennenfent KL, Govindan R. Novel formulations of taxanes: a review. Old wine in a new bottle? Ann Oncol 2006;17: 735-49.
Couzin-Frankel J. Breakthrough of the year 2013. Cancer immunotherapy. Science 2013;342: 1432-3.
Brahmer JR, Hammers H, Lipson EJ. Nivolumab: targeting PD-1 to bolster antitumor immunity. Future Oncol 2015;11: 1307-26.
Brahmer J, Reckamp KL, Baas P, Crino L, Eberhardt WE, Poddubskaya E, Antonia S, Pluzanski A, Vokes EE, Holgado E, Waterhouse D, Ready N, et al. Nivolumab versus Docetaxel in Advanced Squamous-Cell Non-Small-Cell Lung Cancer. N Engl J Med 2015;373: 123-35.
Larkin J, Hodi FS, Wolchok JD. Combined Nivolumab and ipilimumab or Monotherapy in Untreated Melanoma. N Engl J Med 2015;373: 1270-1.
Motzer RJ, Rini BI, McDermott DF, Redman BG, Kuzel TM, Harrison MR, Vaishampayan UN, Drabkin HA, George S, Logan TF, Margolin KA, Plimack ER, et al. Nivolumab for Metastatic Renal Cell Carcinoma: Results of a Randomized Phase II Trial. Journal of clinical oncology : official journal of the American Society of Clinical Oncology 2015;33: 1430-7.
Li X, Hu W, Zheng X, Zhang C, Du P, Zheng Z, Yang Y, Wu J, Ji M, Jiang J, Wu C. Emerging immune checkpoints for cancer therapy. Acta Oncol 2015;54: 1706-13.
Jiang C, Cai X, Zhang H, Xia X, Zhang B, Xia L. Activity and Immune Correlates of a Programmed Death-1 Blockade Antibody in the treatment of Refractory Solid Tumors. J Cancer 2018;9: 205-12.
Xu-Monette ZY, Zhang M, Li J, Young Kh. PD-1/PD-L1 Blockade: Have We Found the Key to Unleash the Antitumor Immune Response? Front Immunol 2017;8: 1597.
Torphy RJ, Schulick RD, Zhu Y. Newly Emerging Immune Checkpoints: Promises for Future Cancer Therapy. Int J Moll Sci 2017;18.
They L, Michaud HA, Becquart O, Lafont V, Guillot B, Boissiere-Michot F, Jarlier M, Mollevi C, Ellaou JF, Bonnefoy N, Gros L. PD-1 blockade at the time of tumor escape potentiates the immune-mediated antitumor effects of a melanomatargeting monoclonal antibody. Oncoimmunology 2017;6: e1353857.
Nomi T, Sho M, Akahori T, Hamada K, Kubo A, Kanehiro H, Nakamura S, Enomoto K, Yagita H, Azuma M, Nakajima Y. Clinical significance and therapeutic potential of the programmed death-1 ligand/programmed death-1 pathway in human pancreatic cancer. Clinical cancer research : an official journal of the American Association for Cancer Research 2007;13: 2151-7.
Okudaira K, Hokari R, Tsuzuki Y, Okada Y, Komoto S, Watanabe C, Kurihara C, Kawaguchi A, Nagao S, Azuma M, Yagita H, Miura S. Blockade of B7-H1 or B7-DC induces an anti-tumor effect in a mouse pancreatic cancer model. Int J Oncol 2009;35: 741-9.
Brahmer JR, Drake CG, Wollner I, Powderly JD, Picus J, Sharfman WH, Stankevich E, Pons A, Salay TM, McMiller TL, Gilson MM, Wang C, et al. Phase I study of single-agent anti-programmed death-1 (MDX-1106) in refractory solid tumors: safety, clinical activity, pharmacodynamics, and immunologic correlates. Journal of clinical oncology : official journal of the American Society of Clinical Oncology 2010;28: 3167-75.
Brahmer JR, Tykodi SS, Chow LQ, Hwu WJ, Topallan SL, Hwu P, Drake CG, Camacho LH, Kauh J, Odunsi K, Pitot HC, Hamid O, et al. Safety and activity of anti-PD-L1 antibody in patients with advanced cancer. N Engl J Med 2012;366: 2455-65.
Le DT, Lutz E, Uram JN, Sugar EA, Onners B, Solt S, Zheng L, Diaz LA, Jr., Donehower RC, Jaffee EM, Laheru DA. Evaluation of ipilimumab in combination with allogeneic pancreatic tumor cells transfected with a GM-CSF gene in previously treated pancreatic cancer. J Immunother 2013;36: 382-9.
Lutz ER, Wu AA, Bigelow E, Sharma R, Mo G, Soares K, Solt S, Dorman A, Warnwea A, Yager A, Laheru D, Wolfgang CL, et al. Immunotherapy converts nonimmunogenic pancreatic tumors into immunogenic foci of immune regulation. Cancer Immunol Res 2014;2: 616-31.
Ghebeh H, Lehe C, Barhoush E, Al-Romalh K, Tulbah A, Al-Alwan M, Hendrayani SF, Manogaran P, Alaiya A, Al-Tweigeri T, Aboussekhra A, Dermime S. Doxorubicin downregulates cell surface B7-H1 expression and upregulates its nuclear expression in breast cancer cells: role of B7-H1 as an anti-apoptotic molecule. Breast cancer research : BCR 2010;12: R48.
Peng J, Hamanishi J, Matsumura N, Abiko K, Murat K, Baba T, Yamaguchi K, Horikawa N, Hosoe Y, Murphy SK, Konishi I, Mandal M. Chemotherapy Induces Programmed Cell Death-Ligand 1 Overexpression via the Nuclear FactorkappaB to Foster an Immunosuppressive Tumor Microenvironment in Ovarian Cancer. Cancer research 2015;75: 5034-45.
Ganta S, Singh A, Rawal Y, Cacaccio J, Patel NR, Kulkarni P, Ferris CF, Amiji MM, Coleman TP. Formulation development of a novel targeted theranostic nanoemulsion of docetaxel to overcome multidrug resistance in ovarian cancer. Drug Deliv 2016;23: 968-80.
Maude SL, Frey N, Shaw PA, Aplenc R, Barrett DM, Bunin NJ, Chew A, Gonzalez VE, Zheng Z, Lacey SF, Mahnke YD, Melenhorst JJ, et al. Chimeric antigen receptor T cells for sustained remissions in leukemia. N Engl J Med 2014;371: 1507-17.
Schiff PB, Horwitz SB. Taxol stabilizes microtubules in mouse fibroblast cells. Proc Natl Acad Sci U S A 1980;77: 1561-5.
Jordan MA, Toso RJ, Thrower D, Wilson L. Mechanism of mitotic block and inhibition of cell proliferation by taxol at low concentrations. Proc Natl Acad Sci U S A 1993;90: 9552-6.
Bocci G, Danesi R, Di Paolo AD, Innocenti F, Allegrini G, Falcone A, Melosi A, Battistoni M, Barsanti G, Conte PF, Del Tacca M. Comparative pharmacokinetic analysis of 5-fluorouracil and its major metabolite 5-fluoro-5,6-dihydrouracil after conventional and reduced test dose in cancer patients. Clinical cancer research : an official journal of the American Association for Cancer Research 2000;6: 3032-7.
Sakai H, Kokura S, Ishikawa T, Tsuchiya R, Okajima M, Matsuyama T, Adachi S, Katada K, Kamada K, Uchiyama K, Handa O, Takagi T, et al. Effects of anticancer agents on cell viability, proliferative activity and cytokine production of peripheral blood mononuclear cells. J Clin Biochem Nutr 2013;52: 64-71.
Okino H, Maeyama R, Manabe T, Matsuda T, Tanaka M. Transtissue, sustained release of gemcitabine from photocured gelatin gel inhibits the growth of heterotopic human pancreatic tumor in nude mice. Clinical cancer research : an official journal of the American Association for Cancer Research 2003;9: 5786-93.

(56) References Cited

OTHER PUBLICATIONS

Pardoll DM. The blockade of immune checkpoints in cancer immunotherapy. Nature reviews Cancer 2012;12: 252-64.

Freeman GJ, Long AJ, Iwai Y, Bourque K, Chernova T, Nishimura H, Fitz LJ, Malenkovich N, Okazaki T, Byrne MC, Horton HF, Fouser L, et al. Engagement of the PD-1 immunoinhibitory receptor by a novel B7 family member leads to negative regulation of lymphocyte activation. J Exp Med 2000;192: 1027-34.

Nishimura H, Honjo T. PD-1: an inhibitory immunoreceptor involved in peripheral tolerance. Trends Immunol 2001;22: 265-8.

Okazaki T, Maeda A, Nishimura H, Kurosaki T, Honjo T. PD-1 immunoreceptor inhibits B cell receptor-mediated signaling by recruiting src homology 2-domain-containing tyrosine phosphatase 2 to phosphotyrosine. Proc Natl Acad Sci U S A 2001;98: 13866-71.

Iwai Y, Terawaki S, Honjo T. PD-1 blockade inhibits hematogenous spread of poorly immunogenic tumor cells by enhanced recruitment of effector T cells. Int Immunol 2005;17: 133-44.

Hirano F, Kaneko K, Tamura H, Dong H, Wang S, Ichikawa M, Rietz C, Flies DB, Lau JS, Zhu G, Tamada K, Chen L. Blockade of B7-H1 and PD-1 by monoclonal antibodies potentiates cancer therapeutic immunity. Cancer research 2005;65: 1089-96.

Lukens JR, Cruise MW, Lassen MG, Hahn YS. Blockade of PD-1/B7-H1 interaction restores effector CD8+ T cell responses in a hepatitis C virus core murine model. J Immunol 2008;180: 4875-84.

Guiducci C, Vicari AP, Sangaletti S, Trinchieri G, Colombo MP. Redirecting in vivo elicited tumor infiltrating macrophages and dendritic cells towards tumor rejection. Cancer research 2005;65: 3437-46.

\* cited by examiner

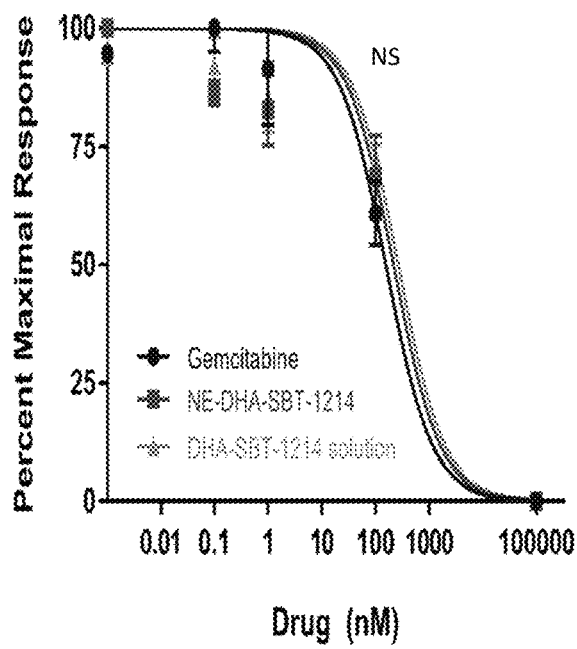
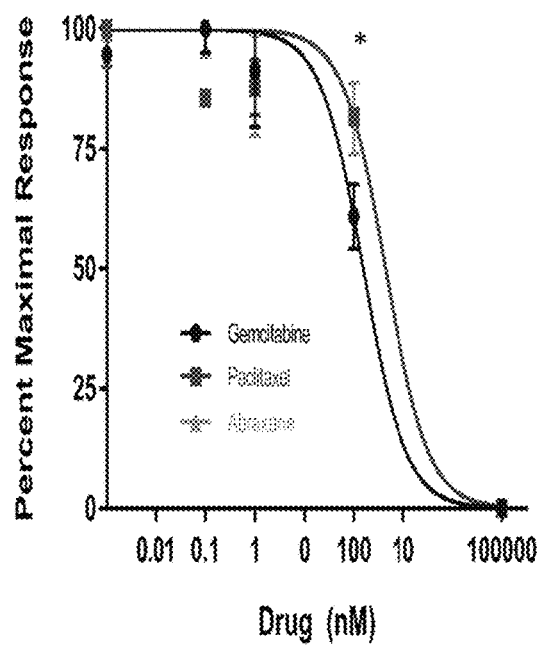
| Drug | IC50 (nM) (±S.D.) | P-value |
|---|---|---|
| Gemcitabine | 154.6 ± 63.2 | - |
| NE-DHA-SBT-1214 | 215.1 ± 96.5 | 0.373 |
| DHA-SBT-1214 solution | 262.8 ± 34.8 | 0.0930 |
FIGURE 5A
| Drug | IC50 (nM) (±S.D.) | P-value |
|---|---|---|
| Gemcitabine | 154.6 ± 63.2 | - |
| Paclitaxel | 443.9 ± 183.0 | 0.0459 |
| Abraxane | 428.2 ± 163.8 | 0.0501 |
FIGURE 5B

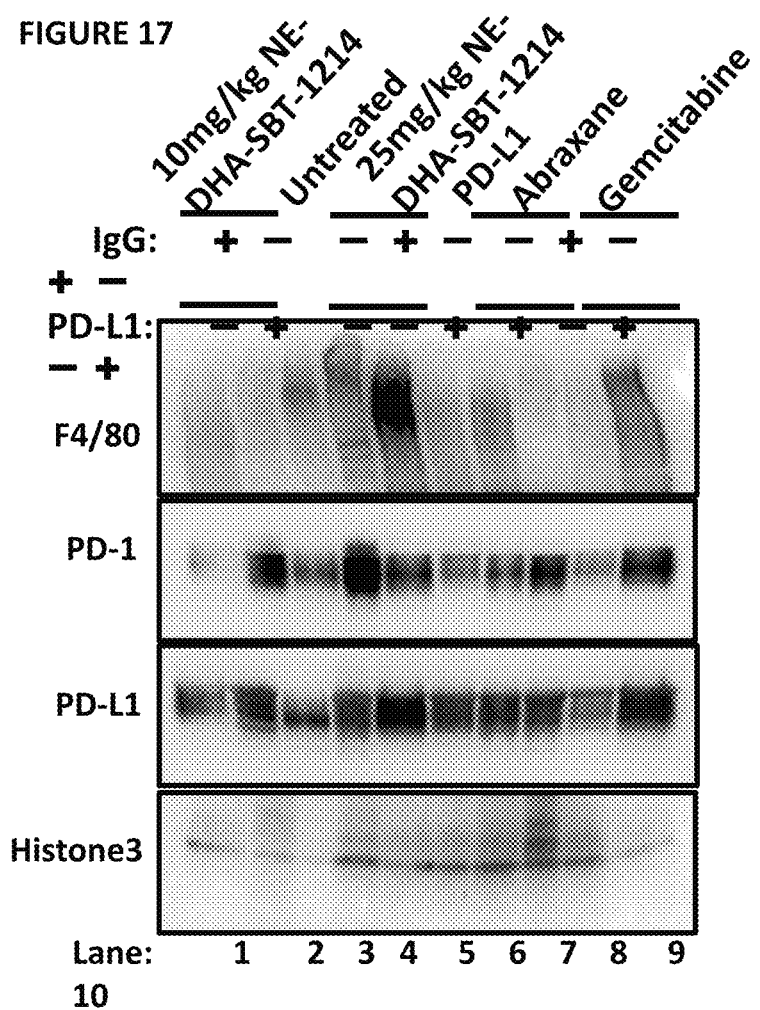

| FIGURE 18A | FIGURE 18B | FIGURE 18C | FIGURE 18D | FIGURE 18E |
|---|---|---|---|---|
| Untreated | PD-L1 | Abraxane+IgG | Abraxane+PD-L1 | Gemcitabine+IgG |
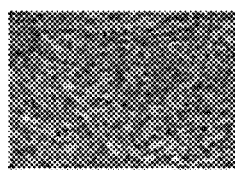 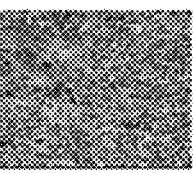 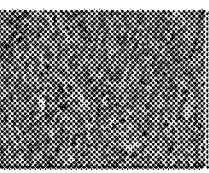 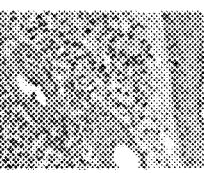 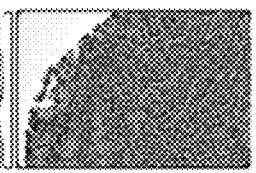
| | 10mg/kg | 10mg/kg | 25mg/kg | 25mg/kg |
|---|---|---|---|---|
| Gemcitabine+PD-L1 | NE-DHA-SBT-1214+IgG | NE-DHA-SBT-1214+PD-L1 | NE-DHA-SBT-1214+IgG | NE-DHA-SBT-1214+PD-L1 |
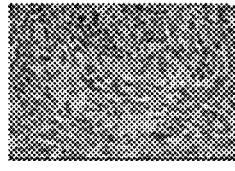  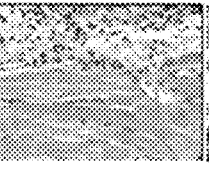 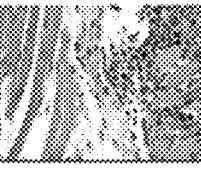 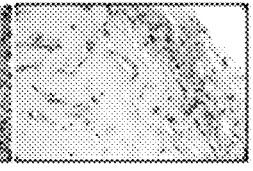
| FIGURE 18F | FIGURE 18G | FIGURE 18H | FIGURE 18I | FIGURE 18J |

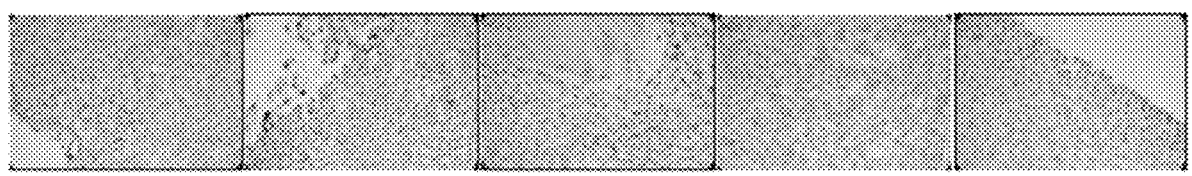

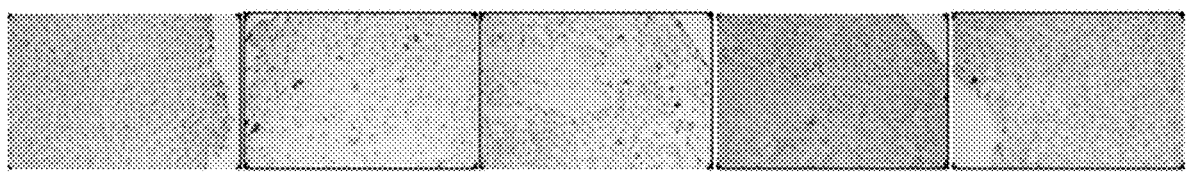
FIGURE 20A Untreated  FIGURE 20B PD-L1  FIGURE 20C Abraxane+IgG  FIGURE 20D Abraxane+PD-L1  FIGURE 20E Gemcitabine+IgG
FIGURE 20F Gemcitabine+PD-L1  FIGURE 20G 10mg/kg NE-DHA-SBT-1214+IgG  FIGURE 20H 10mg/kg NE-DHA-SBT-1214+PD-L1  FIGURE 20I 25mg/kg NE-DHA-SBT-1214+IgG  FIGURE 20J 25mg/kg NE-DHA-SBT-1214+PD-L1

| FIGURE 21A | FIGURE 21B | FIGURE 21C | FIGURE 21D | FIGURE 21E |
|---|---|---|---|---|
| Untreated | PD-L1 | Abraxane+IgG | Abraxane+PD-L1 | Gemcitabine+IgG |
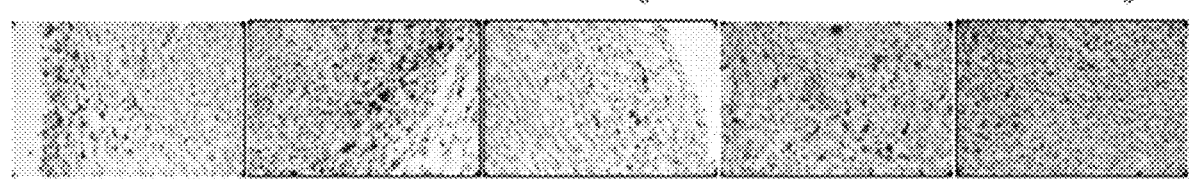
| | 10mg/kg | 10mg/kg | 25mg/kg | 25mg/kg |
|---|---|---|---|---|
| Gemcitabine+PD-L1 | NE-DHA-SBT-1214+IgG | NE-DHA-SBT-1214+PD-L1 | NE-DHA-SBT-1214+IgG | NE-DHA-SBT-1214+PD-L1 |
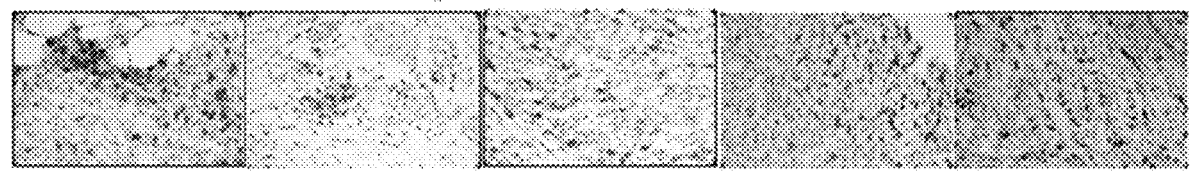
| FIGURE 21F | FIGURE 21G | FIGURE 21H | FIGURE 21I | FIGURE 21J |
|---|---|---|---|---|

COMBINATION TAXOID NANOEMULSION WITH IMMUNOTHERAPY IN CANCER

GRANT INFORMATION

This invention was made with government support under CA103314, CA132396, and HHSN261201500018C awarded by the National Institutes of Health. The government has certain rights in the invention.

BACKGROUND OF THE INVENTION

1. Technical Field

The present invention relates to treatments for cancer, especially multi-drug resistant cancers. More specifically, the present invention relates to combination treatments of taxoids and immunotherapy.

2. Background Art

PD-1 and PD-L1 inhibitors are immune checkpoint inhibitors that are used to treat various forms of cancer. Unfortunately, PD-L1 expression by tumor cells, which may be one of the important parameters that correlates with and may even be required for efficacy of PD-1/PD-L1 inhibitors, varies by tumor type and among individual patients (see, e.g., Taube et al., Clin Cancer Res; 20(19): 5064-74 (2014) and Sunshine and Taube, Current Opinion in Pharmacology, 23:32-38 (2015)). CTLA-4 inhibitors are also checkpoint inhibitors that are being developed to treat various forms of cancer. CTLA-4 expression has also been shown to correlate with efficacy of CTLA-4 inhibitors.

Pancreatic ductal adenocarcinoma (PDAC) is a lethal and aggressive disease with the lowest 5-year patient survival rate of any tumor type routinely tracked (6%). The incidence of PDAC is rising, and it is projected to become the second leading cause of cancer-related death in the United States by 2025. PDAC is distinguished by a dense desmoplastic stroma, rich in fibroblasts, extracellular matrix, and inflammatory leukocytes (but few infiltrating effector T cells). Although certain combination chemotherapies are increasingly effective for PDAC, tumor response rates remain low and durability is short. The presence of cancer initiating or stem cells (CSCs) as a subpopulation in human pancreatic tumor has been confirmed and the CSC's have been attributed to increased tumor growth, invasion and metastasis as well as resistance to chemo and radiation therapy. Elaborate desmoplastic extracellular matrix of PDAC, rich in collagen and hyaluronic acid, severely distorts the vasculature and lymphatic drainage within the tumor resulting in decreased perfusion and increased interstitial fluid pressure. Vascular dysfunction, therefore, is another hallmark property of PDAC that limits the ability to penetrate into and deliver drugs to the deeply seated cancer cells within the tumor mass. Vascular dysfunction is further related to sub-optimal oxygen availability within the tumor, giving rise to a hypoxic microenvironment that has been implicated in imparting resistance to chemo and radiotherapy as well as increasing the invasiveness and metastatic potential of the cancer cells. A hypoxic environment harbors highly drug-resistant, quiescent cells that show CSC-like traits and, therefore, this sub-population of stem cells are important targets for therapy to effectively treat the disease and to address clinical recurrences. All of these factors working in tandem present an insurmountable obstacle in designing a safe and effective therapy against PDAC.

For about two decades now, gemcitabine has been the mainstay of chemotherapy for PDAC. A randomized Phase III trial demonstrated the superiority of gemcitabine over 5-flurouracil (5-FU) in quality of life and median overall survival from 4.41 months to 5.65 months. Following this study, multiple trials have been conducted with various combinations of chemotherapy agents with gemcitabine. Unfortunately, until recently, most of these trials were disappointingly negative with a few exceptions. The first Phase III clinical trial to show a markedly improved overall survival was reported in a new combination therapy with leucovorin-modulated 5-fluorouracil, irinotecan, and oxaliplatin (FOLFIRINOX) yielding a median survival of 11.1 months. FOLFIRINOX regimen, however, is associated with significant toxicities, which includes neutropenia, diarrhea, and sensory neuropathy, limiting its use to only patients with good performance status. Another new combination gemcitabine regimen with nanoparticle albumin bound (nab)-paclitaxel (ABRAXANE®) was introduced in the Metastatic Pancreatic Adenocarcinoma Trial (MPACT) Phase III clinical trial. Gemcitabine plus ABRAXANE® increased the median overall survival to 8.7 months as compared to 6.6 months with gemcitabine monotherapy. Additionally, gemcitabine plus (nab)-paclitaxel has less toxicity as compared to FOLFIRINOX, making it the most widely used regimen in the community setting for patients with newly diagnosed metastatic pancreatic cancer (PC) in the United States. However, despite the improvements made with the two newer regimens—FOLFIRINOX and gemcitabine with (nab)-paclitaxel—the progression free survival in both regimens remains dismal. Many patients treated with either of the two regimens have ultimately relapsed and require second line therapy. In addition, new immuno-oncology "IO" agents, such as anti-PD-1 or anti CTLA-4 antibody therapies, have not shown efficacy in PDAC due to a highly immunosuppressive microenvironment and dense stroma that inhibits T-cell infiltration in the tumor mass. As such, there is a critical unmet need in aggressive and refractory PDAC to develop better therapeutic options that can improve on the dismal survival statistics.

The lack of optimum therapeutic effect in PDAC has been associated with both tumor-acquired resistance after initial treatment in addition to the re-population of the tumor from CSC seeds. An ideal drug to provide in a combination treatment regimen would be one that both de-bulks the tumor as well as targets the cancer stem cell population. One of the advantages of drugs like paclitaxel is that they target tubulin/microtubule, a basic component of the cell that is absolutely necessary for cell survival; however, resistance can be achieved by up-regulation of multi-drug resistance (MDR) mechanisms such as efflux pumps or by tubulin mutations. Accordingly, a continuing challenge in cancer chemotherapy is to develop new cytotoxic agents with greater selectivity for the tumor, overcoming MDR, improved pharmacology and a reduction in toxicity.

One of the next-generation taxoids, such as DHA-SBT-1214, addresses these issues. It has several unique properties that make it a potentially useful therapy in the clinic either as a stand-alone treatment or in combination with other therapeutic modalities. DHA-SBT-1214 is active against many drug resistant tumor types and is not a substrate for several MDR mechanisms, such as over-expression of the P-glycoprotein (P-gp) transporter and the treatment results in complete tumor regression in pancreatic, colon and prostate cancer xenograft models. DHA-SBT-1214, exhibited two-to-three orders of magnitude higher potency than those of paclitaxel and docetaxel against drug-resistant cell lines expressing MDR phenotypes. Secondly, DHA-SBT-1214, has been shown to down-regulate stem related genes in CSCs purified from three human colon cancer cell lines, DLD-1, HTC-116, and HT-29. DHA-SBT-1214 was effective in a patient-derived prostate cancer stem cell xenograft model, where paclitaxel was completely ineffective and ABRAXANE® only marginally effective in delaying tumor growth and improving survival. Paclitaxel and docetaxel are effective initially against breast, ovary, and lung cancers, and show limited efficacy against pancreatic cancer; however human albumin formulated paclitaxel has shown some benefit. PDAC is inherently refractory due to the over expression of Pgp, an effective ATP-binding cassette (ABC transporter), which effluxes hydrophobic anticancer agents including paclitaxel and docetaxel. In sharp contrast to paclitaxel, DHA-SBT-1214 shows remarkable activity against drug-resistant cancer cells, expressing MDR phenotypes including PDAC cells and tumor xenografts. Accordingly, there is every indication that DHA-SBT-1214 a powerful tumor-targeting chemotherapeutic agent, overcoming the weaknesses of paclitaxel, docetaxel and ABRAXANE® and substantially improve the quality of life of PDAC patients.

For the development of DHA-SBT-1214 and other taxoids as a therapeutic for clinical treatment of PDAC, several important considerations must be met. First, since these drugs are very hydrophobic, a safe formulation that can solubilize the molecule and afford systemic delivery potential is needed. Second, the DHA molecule linked through an ester bond is susceptible to cleavage in the aqueous environment and especially in the presence of esterases. Third, it is important to decrease off-target effects of the taxoids by enhancing targeted delivery to the tumor mass. Based on these requirements, we have developed an omega-3 rich fish oil containing oil-in-water nanoemulsion formulation and have evaluated the biodistribution and pharmacokinetics of the drug in comparison with the solution formulation using both naïve and PPT-2 human prostate tumor bearing mice.

Nanoemulsions are heterogenous systems composed of oil in water where the oil droplets are reduced to nanometer size using either ultrasound or high-pressure homogenization methods. The surface of the oil droplets is decorated with amphiphilic molecules to lower the interfacial tension and afford stability in the presence of aqueous medium. DHA-SBT-1214 can be encapsulated in the oil droplet of the nanoemulsion and is protected from hydrolysis by esterases. Surface modification of the oil droplet with poly(ethylene glycol) (PEG) prolongs the circulation half-life upon systemic administration and passive targeting to solid tumors due to the leaky vasculature by the enhanced permeability and retention (EPR) effect. Additionally, there is evidence that suggests higher accumulation of omega-3 rich oils in tumors and that could also provide additional selectivity in delivery of the taxoids to the tumor mass upon systemic administration.

The treatment of cancer has recently been significantly advanced with the emergence of cancer immunotherapy. The check-point inhibitors (CIs) have now been established as a fundamental new modality to treat cancer along with the more established modalities of surgery, radiotherapy and chemotherapy and offer new therapeutic hope for many patients with cancer. Already PD-1 inhibitors pembrolizumab (KEYTRUDA®) and nivolumab (OPDIVA®) have been approved for; first line metastatic melanoma, metastatic melanoma that has failed therapy with a B-raf inhibitor or Ipilimumab and treatment of non-small cell lung cancer that has failed a platinum-based therapy. Recently pembrolizumab has been approved for second-line treatment of renal cancer and PD-L1 inhibitor durvalumab (IMFINZI®) has received break-through designation for inoperable or recurrent metastatic bladder cancer. Despite the clinical successes, these drugs work only in a minority of patients and have shown a minimal effect in PDAC patients. There is a great deal of effort to identify compounds that can increase the response rates of patients to checkpoint inhibitors and Winograd et al., have shown in murine models that complete resistance to CIs can be overcome by combining with chemotherapy agents such as ABRAXANE®. There is significant positive evidence, including Applicants' own data that shows taxoid effects in promoting anti-tumor immunological effects through increased expression of targets and T-cell infiltration. Taxane treatment has been shown to stimulate tumor-associated macrophage cytotoxicity, induce the activation of dendritic cells, natural killer cells, tumor specific cytotoxic T-cells as well as downregulate regulatory T cells ("$T_{regs}$"). It has also been shown to inhibit myeloid-derived suppressor cell function. Combining such approaches with anti-PD-L1/PD-1 therapies will broaden the clinical benefit to include a greater proportion of patients.

Based on the preliminary evidence presented, NE-DHA-SBT-1214 provides a unique opportunity to both de-bulk the tumor and kill cancer stem cells thus creating an unprecedented path forward to combine with IO agents. The temporal sequencing of the combination of NE-DHA-SBT-1214 and IO therapy will be important in uncovering the potential synergistic effects of this combination therapy. By de-bulking the tumor and affecting stromal permeability, we are potentially releasing antigen into the system and by killing cancer stem cells we are both releasing cancer stem cell antigens, as well as, decreasing the re-population effect of these cells. An additional effect of de-bulking tumor is that you are decreasing the level of inherent immune suppression of the tumor (e.g., reduction in the number of tumor cells releasing immune suppressive cytokines and immune suppressive ligands). De-bulking also enhances T-cell permeability into the tumor interstitium, which is a profound barrier in PDAC, due to the presence of desmoplastic stroma.

There remains a need for more effective cancer treatments and a need to enhance the effectiveness of immunology agents in cancer treatment.

SUMMARY OF THE INVENTION

The present invention provides for a composition of an omega-3 polyunsaturated fatty acid (PUFA)-taxoid conjugate formulated in an oil-in-water nanoemulsion (NE) drug delivery system in combination with an immune-oncology (IO) agent to enhance therapeutic efficacy in refractory cancers, such as PDAC.

The present invention also provides for a method of treating cancer, by administering an effective amount of a pharmaceutical composition including an omega-3 PUFA-taxoid conjugate in combination with an IO agent encapsulated in an NE drug delivery system to a subject in need of treatment, and treating cancer.

DESCRIPTION OF THE DRAWINGS

Other advantages of the present invention are readily appreciated as the same becomes better understood by reference to the following detailed description when considered in connection with the accompanying drawings wherein:

FIGS. 5A and 5B are graphs of the activity of different anti-cancer agents against Panc02 cells;

FIG. 10A shows tumors from mice treated with vehicle, FIG. 10B shows tumors from PD-L1 (200 μg) treated mice, FIG. 10C and FIG. 10D show tumors from ABRAXANE™ plus IgG or PD-L1 (200 μg) treated mice respectively, FIG. 10E shows tumors from NE-DHA-SBT-1214 (10 mg/kg) plus IgG (200 μg) treated mice, FIG. 10F and FIG. 10G show tumors from Gemcitabine plus IgG or PD-L1 (200 μg) treated mice respectively, FIG. 10H shows tumors from NE-DHA-SBT-1214 (10 mg/kg) plus PD-L1 (200 μg) treated mice, and FIG. 10I and FIG. 10J show tumors from NE-DHA-SBT-1214 plus IgG or PD-L1 (200 μg) treated mice respectively;

FIG. 17 shows tumor tissue lysate from different treated groups prepared and protein level of different proteins analyzed using western blotting;

FIGS. 18A-18J show histopathological evaluation of the Panc02-induced tumor tissues collected from control and different combination treated mice (hematoxylin & eosin staining), FIG. 18A is untreated, FIG. 18B is PD-L1, FIG. 18C is ABRAXANE™+IgG, FIG. 18D is ABRAXANE™+PD-L1, FIG. 18E is Gemcitabine+IgG, FIG. 18F is Gemcitabine+PD-L1, FIG. 18G is 10 mg/kg NE-DHA-SBT-1214+IgG, FIG. 18H is 10 mg/kg NE-DHA-SBT-1214+PD-L1, FIG. 18I is 25 mg/kg NE-DHA-SBT-1214+IgG, and FIG. 18J is 25 mg/kg NE-DHA-SBT-1214+PD-L1;

FIG. 19A-19J show analysis of infiltrating CD4 cells by immunohistochemistry, FIG. 19A is untreated, FIG. 19B is PD-L1, FIG. 19C is ABRAXANE™+IgG, FIG. 19D is ABRAXANE™+PD-L1, FIG. 19E is Gemcitabine+IgG, FIG. 19F is Gemcitabine+PD-L1, FIG. 19G is 10 mg/kg NE-DHA-SBT-1214+IgG, FIG. 19H is 10 mg/kg NE-DHA-SBT-1214+PD-L1, FIG. 19I is 25 mg/kg NE-DHA-SBT-1214+IgG, and FIG. 19J is 25 mg/kg NE-DHA-SBT-1214+PD-1;

FIG. 20A-20J show analysis of infiltrating CD8 cells by immunohistochemistry, FIG. 20A is untreated, FIG. 20B is PD-L1, FIG. 20C is ABRAXANE™+IgG, FIG. 20D is ABRAXANE™+PD-L1, FIG. 20E is Gemcitabine+IgG, FIG. 20F is Gemcitabine+PD-L1, FIG. 20G is 10 mg/kg NE-DHA-SBT-1214+IgG, FIG. 20H is 10 mg/kg NE-DHA-SBT-1214+PD-L1, FIG. 20I is 25 mg/kg NE-DHA-SBT-1214+IgG, and FIG. 20J is 25 mg/kg NE-DHA-SBT-1214+PD-L1; and FIG. 21A-21J show analysis of infiltrating PD1 cells by immunohistochemistry, FIG. 21A is untreated, FIG. 21B is PD-L1, FIG. 21C is ABRAXANE™+IgG, FIG. 21D is ABRAXANE™+PD-L1, FIG. 21E is Gemcitabine+IgG, FIG. 21F is Gemcitabine+PD-L1, FIG. 21G is 10 mg/kg NE-DHA-SBT-1214+IgG, FIG. 21H is 10 mg/kg NE-DHA-SBT-1214+PD-L1, FIG. 21I is 25 mg/kg NE-DHA-SBT-1214+IgG, and FIG. 21J is 25 mg/kg NE-DHA-SBT-1214+PD-1.

DETAILED DESCRIPTION OF THE INVENTION

Figure 1:
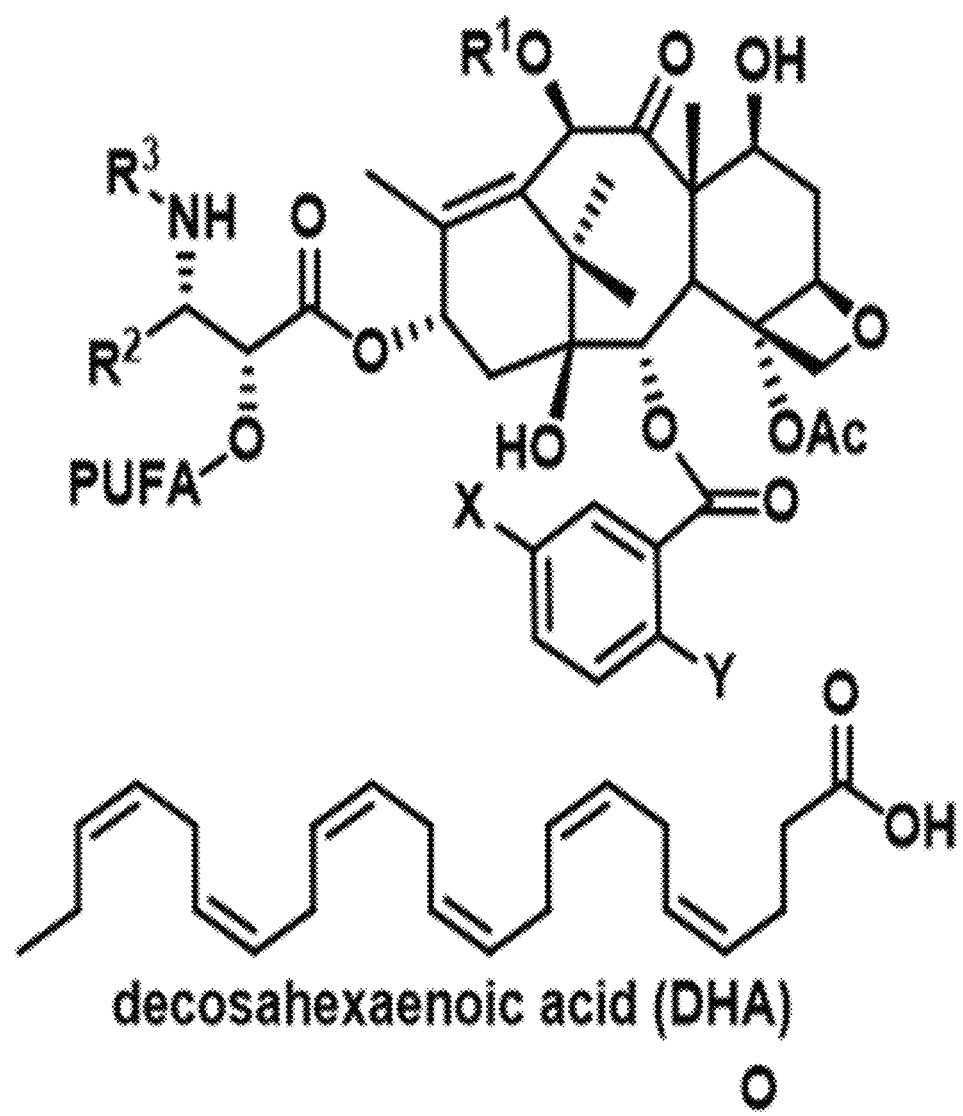
FIG. 1 is a depiction of the molecule DHA-SBT-1214.

The present invention is generally directed to compositions for treating cancer. The composition is preferably an omega-3 polyunsaturated fatty acid (PUFA)-taxoid conjugate formulated in an oil-in-water nanoemulsion (NE) drug delivery system in combination with an immune-oncology (IO) agent. The preferred embodiment is NE-DHA-SBT-1214, in which the PUFA-taxoid conjugate is DHA-SBT-1214, whose structure is shown in FIG. 1, in combination with anti-PD-L1 antibody.

The term "second-generation taxoid" will be used to refer to a first-generation taxanes, such as paclitaxel (taxol) and docetaxel (taxoid), in which (i) the C-3'-phenyl group is replaced with an alkenyl or alkyl group and (ii) the C-10 position is modified with certain acyl groups, and a C-3'N position is a t-Boc group. The term "PUFA-taxoid conjugate" will be used to refer to a taxoid conjugated to a polyunsaturated fatty acid (PUFA) at the C2' position. PUFA-taxoid conjugates are characterized by their ability to be preferentially accumulated in tumor and stay for long time, while exhibiting impressive efficacy especially against multidrug-resistant tumors (Ojima, I., Taxoid-Fatty Acid Conjugates and Pharmaceutical Compositions Thereof for Treatment of Cancer", U.S. Pat. No. 7,820,839 B2, Oct. 26, 2010).

The term "nanoemulsion" (NE) will be used to refer to an oil-in-water emulsion with mean droplet diameters ranging from 50 to 1000 nm, with a diameter of >200 nm being preferred. The preferred NE oil phase is prepared as in U.S. Patent Application Publication US20070148194 to Amiji, et al. using omega-3 fatty acid-rich edible oils, such as fish oil or flax-seed oil. Other oils can be used such as, but not limited to, pine nut oil, safflower oil, primrose oil, black currant oil, borage oil, wheat germ oil, chia oil, hemp oil, perilla oil, grape oil, squalene oil, and fungal oil. The oil droplet is modified with surfactants, including phospholipids (e.g., LIPOID®) and poly(ethylene oxide)-containing non-ionic surfactants (e.g., Pluronic or Tween). The surface of the oil droplet can also be modified for selective targeting to tumor cells with a targeting agent, including the use of folate, EGFR peptide, and other known targeting ligands. The composition can also contain image contrast agents, including fluorophores, MRI contrast agents, or radioactive compounds.

The term "immuno-oncology agent" or "IO agent" as used herein refers to any agent that targets the body's immune system to provide a response to cancer. Many cancer cells have tumor-associated antigens that can be recognized by the body's immune system, and these antigens can be targeted in active immunotherapy. Passive immunotherapies can enhance the body's existing antitumor responses. An essential role of the immune system is protecting the body against the proliferation of malignant cells. Immune modulation is increasingly seen as pivotal to the treatment of many cancers. Regulatory approval has been achieved for several new cancer immunotherapies, and many others are in the developmental pipeline. In particular, the degree of immune infiltration and the ratio of effector T cells to regulatory T cells have been shown to be robust prognostic factors, regardless of therapy, in multivariate analyses in many different types of cancers. Cancers with high levels of immune infiltrate generally progress more slowly. Methodologies are now being validated for reproducible quantitation of immune infiltration.

Several immunosuppression pathways are known to prevent T cells from effectively infiltrating malignancies and/or to suppress the function of infiltrating lymphocytes. These pathways include (1) generation of dysfunctional antigen-presenting cells; (2) polarization of the immune system toward a Th2 response, a less effective pathway for immune rejection of cancer; (3) induction of immune regulatory cells such as regulatory T cells and myeloid-derived suppressor cells; (4) induction or secretion of immunosuppressive cytokines such as IL10 and transforming growth factor (TGF); and (5) induction of T-cell anergy or T-cell exhaustion. This spectrum of immunosuppressive pathways that may delay or prevent the host response to tumor cells, allowing tumor progression and ultimately killing the patient, represents a highly complex diagnostic and therapeutic challenge to the safe, effective, and appropriate implementation of targeted immunomodulatory cancer therapies. An added difficulty is that these immunosuppressive pathways may be induced by functional anti-tumor immune responses.

Agents that can enhance the anti-tumor immune response by modulating both positive and negative regulatory pathways are becoming increasingly important in oncology. Checkpoint inhibitors that "remove the brakes" from effector T cell subsets can mediate significant clinical activity in a number of different cancers. Certain combination immunotherapies that incorporate multiple immune checkpoint inhibitors, or T-cell agonists, are showing even greater activity in clinical trials.

The PUFA in the conjugate is preferably docosahexaenoic acid (DHA) (C-22), but can also be eicosapentaenoic acid (EPA, C-20), or alpha-linolenic acid (LNA, C-18).

The present invention includes formulations of PUFA-taxoid conjugates, which are encapsulated into nanoparticles in NE as disclosed in U.S. Patent Application Publication US20070148194 (2007) to Amiji, et al., which is incorporated herein in its entirety. Alternatively, any taxoid, or combination of taxoids, can be encapsulated in an NE, including, but not limited to, any of the PUFA-taxoid conjugates described in U.S. Pat. No. 7,820,839, to Ojima, and taxoids described in Ojima I and Das M, (2009), both of which are incorporated herein in their entirety.

Other taxoids which can be included in the present invention, as NE formulations include, but are not limited to, paclitaxel, docetaxel, SBT-1213, SBT-12854, SBT-121303; SBT-1216, SBT-11033, SBT-121313, SBT-121602, cabazitaxel, SBT-1212, SBT-1217, SBT-1102, SBT-1103, SBT-1104, SBT-1106, SBT-1107, SBT-121301, SBT-121302, SBT-121304, SBT-121403, SBT-11031, SBT-11032, SBT-11034, SBT-12851, SBT-12852, SBT-12853, SBT-12855, SBT-12851-1, SBT-12851-3, SBT-12852-1, SBT-12852-3, SBT-12853-1, SBT-12853-3, SBT-12854-1, SBT-12854-3, SBT-12855-1, and SBT-12855-3 (Ojima, et al., 2009). Also included are PUFA-conjugated second generation taxoids, including, but not limited to, DHA-paclitaxel (Bradley, et al., 2001); DHA-docetaxel, DHA-SBT-1213, DHA-SBT-1103, DHA-SBT-1104, DHA-SBT-1216, LNA-SBT-1213, LNA-paclitaxel, LNA-docetaxel, DHA-cabazitaxel, and LNA-cabazitaxel, where LNA=alpha-linolenic acid. Also, DHA or LNA esters of any of the above second-generation taxoids can be used. One skilled in the art can easily make such esters. Working examples of their formulation and effectiveness are found within the indicated references, which are incorporated in their entirety herein.

The IO agent is an agent that uses the individual's immune system to attack and treat cancer, and is most preferably anti-PD-L1 antibody. However, any other IO agent can also be used, such as, but not limited to, anti-PD-1 antibody, ipilumumab (CTLA-4 inhibitor), nivolumab (PD-1 checkpoint inhibitor), pembrolizumab (PD-1 checkpoint inhibitor), atezolizumab (PD-L1 checkpoint inhibitor), pidiluzumab, durvalumab, anti-CD47 antibodies, indoleamine (2,3)-dioxygenase inhibitors, anti-GD2 antibodies, alemtuzumab, ofatumumab, rituximab, or cytokines (interferon-α, interferon-β, interferon-gamma, or interleukins (1-36).

The present invention provides a method of treating cancer, by administering an effective amount of a pharmaceutical composition including a PUFA-taxoid conjugate encapsulated in an NE drug delivery system in combination with an IO agent to a subject in need of treatment, and treating cancer. The combinatorial effect is driven by the ability of the PUFA-taxoid conjugate increasing the expression of PD-L1 in the tumor microenvironment as well causing an increase of both CD4$^+$ and CD8$^+$tumor-infiltrating lymphocytes. These changes in the tumor microenvironment have previously been shown to make patients more responsive to I/O agents in general.

The cancer being treated in the methods herein can be any type of cancer, such as, but not limited to, breast, ovary, lung, head and neck, colon, rectal, pancreatic, melanoma, brain, prostate, leukemia, sarcomas, thyroid, Non-Hodgkin Lymphoma, bladder, gliomas, endometrial, and renal cancer. The PUFA-taxoid conjugate can be any of those described herein, and especially DHA-SBT-1214. Because the PUFA-taxoid conjugate is encapsulated in the NE, it is actively taken up by the body and DHA is cleaved more efficiently than in normal delivery methods. The IO agent is preferably anti-PD-L1 antibody, but can be any IO agent described above. When anti-PD-L1 is administered, the method further includes the step of upregulating PD-L1.

DHA-conjugated SBT-1214 (FIG. 1), exerts a remarkable efficacy against highly drug resistant tumor xenografts in mice, wherein DHA conjugated paclitaxel (TAXOPREXIN®); Luitpold Pharmaceuticals; human Phase I-III clinical trials) paclitaxel, and nab-paclitaxel (ABRAXANE®) do not show meaningful activity. DHA-was linked to SBT-1214, based on the hypothesis that the omega-3 fatty acid conjugate would have the beneficial properties of DHA-paclitaxel (e.g., much reduced toxicity, prolonged residence time in the tumor as compared to paclitaxel, and higher stability in plasma). The DHA conjugation also aids in the incorporation into the omega-3 fatty acid based nanoemulsion, where a 5-fold increase in drug concentration can be achieved. DHA-SBT-1214 shares some activities with paclitaxel such as stabilizing microtubules; however, it has additional anti-tumor mechanisms. The effect of these compounds on the microtubule network is different from those observed with the classical taxanes (docetaxel and paclitaxel), inducing different bundling in cells with microtubules being very short, indicating a very fast nucleation effect and reflecting their high assembly induction power and the ability to inhibit cell division in various cell lines harboring tubulin mutations. DHA-SBT-1214 has been shown to down-regulate many survival genes in three colon cancer stem cell lines and activate p53 and p21. Taken together, these data suggest that there are several mechanisms that differentiate DHA-SBT-1214 from paclitaxel, docetaxel or ABRAXANE®. The observed remarkable efficacy of DHA-SBT-1214 against several tumor xenografts, especially, Panc-1 and CFPAC-1 (pancreatic) (FIGS. 2 and 3), respectively, as well as CSCs clearly demonstrates that this is not just an incremental improvement, but a profound shift in chemotherapy paradigm.

Figure 2:
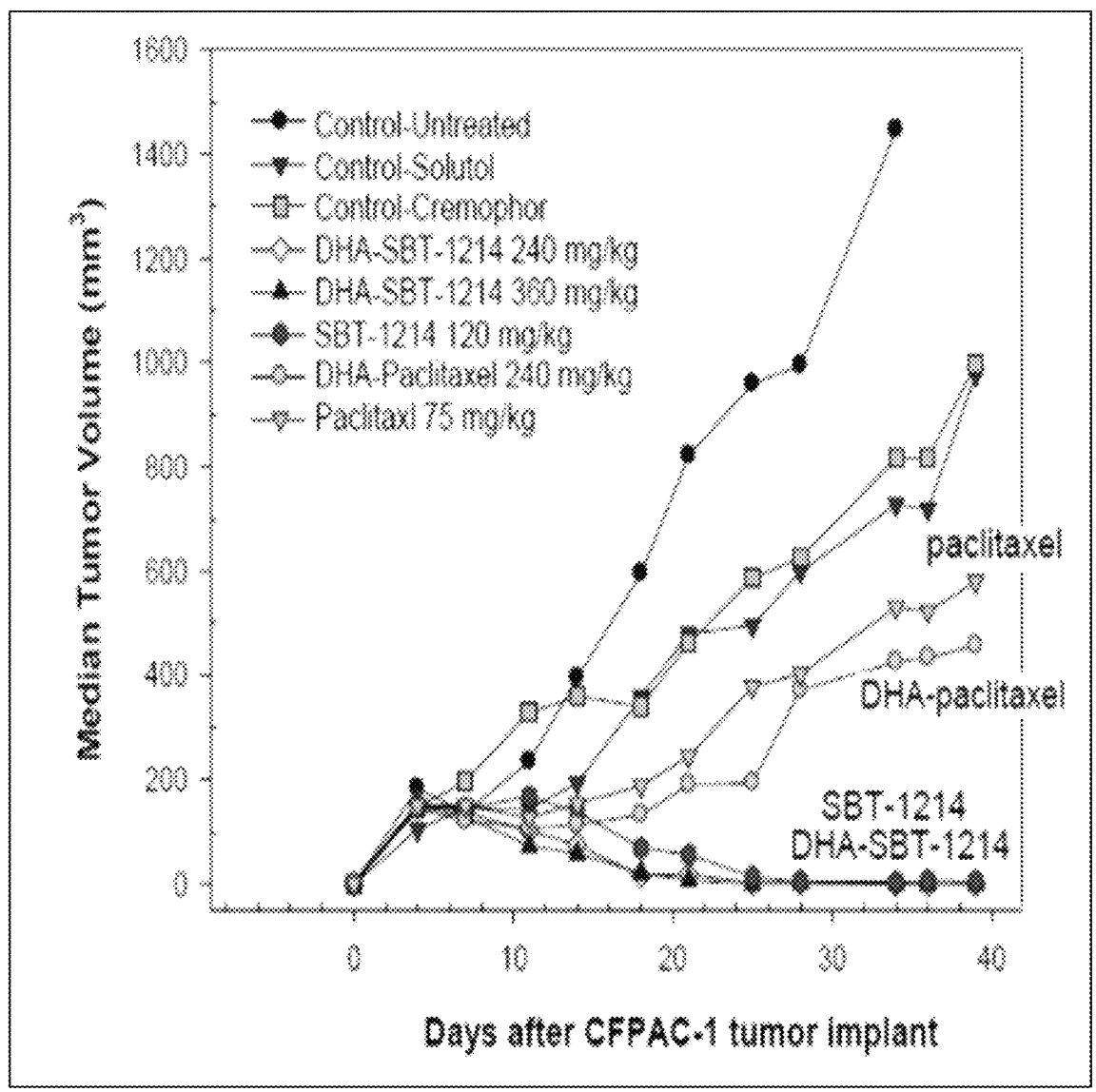
FIG. 2 is a graph of median tumor volume after CFPAC-1 tumor implant.

In FIG. 2, this experiment compared the efficacy of paclitaxel, DHA-paclitaxel and DHA-SBT-1214 using a human CFPAC-1 pancreatic tumor xenograft DHA-SBT-1214 using 240 mg/kg or 300 mg/kg total dose was very effective, causing complete regression and cure for 5 in 5 or 4 in 4, respectively. Paclitaxel and DHA-paclitaxel were much less effective with only minor tumor growth delay as compared to vehicles. SBT-1214 (120 mg/kg total dose) exhibited results superior to paclitaxel with tumor regressions for 6 in 6 mice although only 1 in 6 was cured and appeared to be more toxic than DHA-SBT-1214, showing minor weight loss (<4%) until day 20, while the weight loss was negligible for DHA-SBT-1214 at either the 240 mg/kg or 300 mg/kg total dose.

Figure 3:
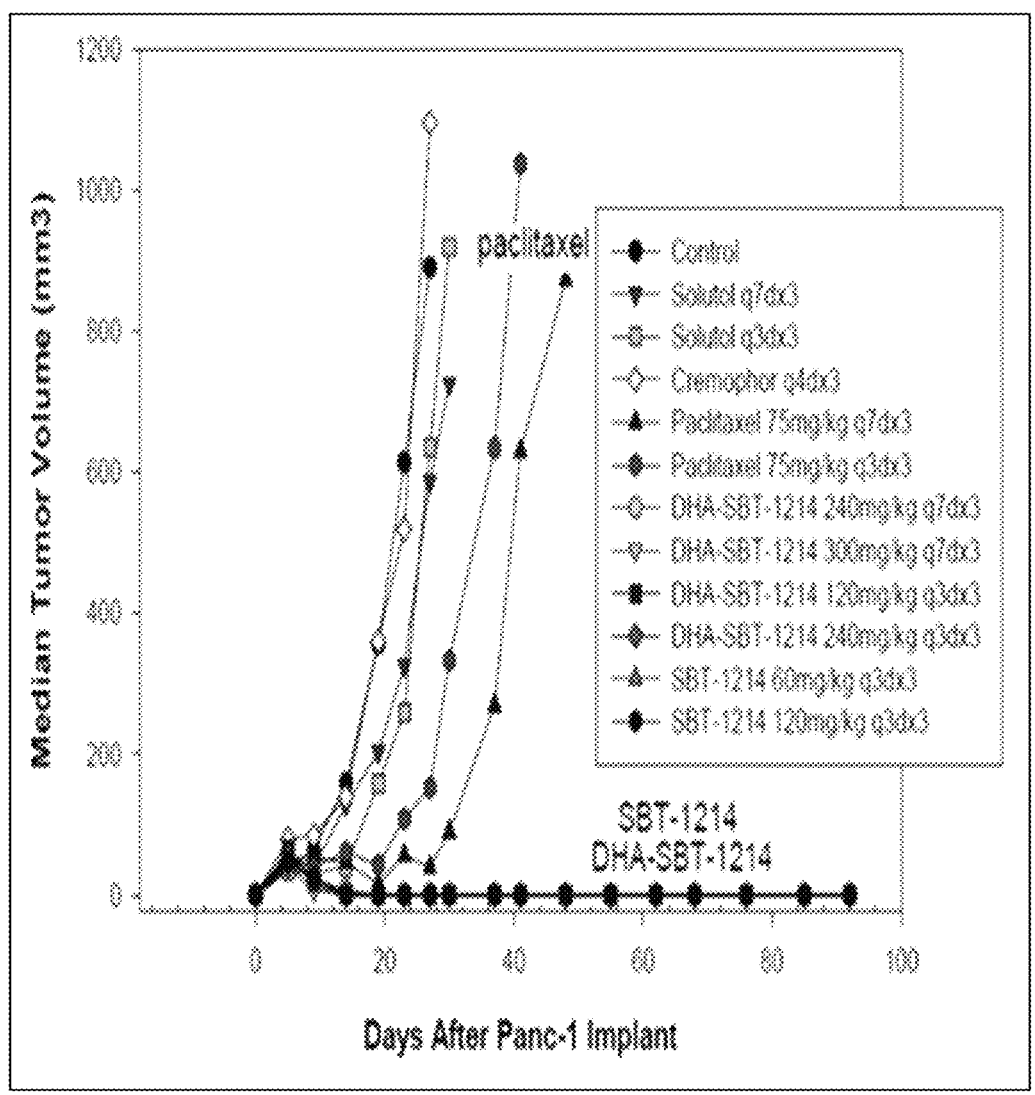
FIG. 3 is a graph of median tumor volume after PANC-1 tumor implant.

In FIG. 3, this experiment compared a q7d×3 with a q3d×3 schedule for paclitaxel and DHA-SBT-1214 using a human PANC-1 pancreatic tumor xenograft in RPCI SCID mice. The results indicated that both schedules were very effective in this human pancreatic tumor xenograft (tumor growth delay >90 days). The MTD for DHA-SBT-1214 appeared to be 240 mg/kg total dosage (80 mg/kg×3 inj=240 mg/kg) with one toxic death occurring at the 300 mg/kg total dose. All mice that received DHA-SBT-1214 achieved CRs and essentially were cured. Paclitaxel was only weakly effective, showing tumor growth delays of 18 days with q7d×3 schedule and 13 days with q3d×3 schedule and no CRs.

The nanoemulsions (NEs) technology developed is simple, versatile, and clinically-translatable colloidal carriers formed by dispersion of PUFA rich edible oils in water and stabilized with an amphiphilic phospholipid monolayer. These NEs have a hydrodynamic diameter of <200 nm, can incorporate considerable amounts of hydrophobic drugs in the high volume fraction of the oil phase, and are suitable for both systemic and oral delivery. The NEs are highly flexible vehicles for the incorporation of drugs and are composed entirely of generally regarded as safe (GRAS) materials, which have highly favorable safety profiles and amenable for large scale GMP manufacturing using high pressure homogenizers, a significant advantage for rapid clinical adoption.

One of the Improvements of the nanoemulsion in the present invention as compared to earlier formulations is how it is taken up the cell. Traditional formulations are taken up by the cell by passive diffusion through the lipid bi-layer. In contrast the nanoemulsion is taken up by receptor-mediated endocytosis, bypassing P-glycoprotein/mdr-1 mediated drug efflux. Once in the cell, ester bond between taxoid and fatty acid tail is cleaved, resulting in the release of an active compound. Applicants have successfully formulated NE-DHA-SBT-1214 with concentrations as high as 30 mg/ml as compared to 6 mg/ml in Tween® 80 or Solutol-HS15. The droplet size is consistently less than 200 nm in diameter allowing one to filter sterilize the final formulation. The zeta potential of the nanoemulsion is in the range of negative 23 mV to 33 m. This is a critical point because the negative charges on the lipid layer ensures that the nanoemulsion droplets do not coalesce and Applicants have stability data for up to a year at 4° C. versus less than 24 hours in Solutol-HS15. Initial toxicology studies have provided a safe and efficacious dose of 25 mg/kg in an aggressive patient-derived xenograft model. The 72 hours $IC_{50}$ of NE-DHA-SBT-1214 against the Panc-1 cell line is 2.3 nM, a 25-fold reduction as compared to Tween-80 formulated DHA-SBT-1214 and the efficacy is at least a 3-fold higher in vivo.

The results from experiments using DHA-SBT-1214 in two human pancreatic tumor models (FIGS. 2 and 3) and a proof-of-concept in patient-derived CSC model are described below. The compelling aspects of DHA-SBT-1214 preclinical activity is its effects on CSCs. Highly plastic CSCs are an important new drug target in the treatment of refractory tumors. Through the development of drugs specifically targeting CSCs (or targeting CSCs in addition to tumor cells) a more durable clinical response may be possible. In addition to the previously described cytotoxicity assays in cell cultures, DHA-SBT-1214 was tested in colon and prostate cancer cell lines grown as spheroids from cells selected for being $CD133^{high}/CD44^{high}$, characteristic of stem cells. In this assay, the number of spheroids was greatly reduced by exposure to DHA-SBT-1214. In addition, DHA-SBT-1214 induced complete regression of drug-resistant colon tumor xenografts in all surviving mice with unusually long-term tumor growth delay (>167 days). Perhaps more significant was the effect of exposure to relatively low concentrations of DHA-SBT-1214 (100 nM to 1 μM) for 24 hours on the expression of genes associated with "stemness" in several colon and prostate cancer cells lines grown as microspheres (6,7). Additionally, NE-DHA-SBT-1214 is superior to ABRAXANE® in a patient-derived PPT2 prostate cancer stem cell xenograft model, and equally effective in pancreatic cancer organoids.

In studies with DHA-SBT-1214 and prostate cancer stem cells, Applicants previously determined that low concentrations of DHA-SBT-1214 (0.1-1 μM) induced up to 80-90% death of the highly tumorigenic and highly drug-resistant prostate CD133+ cells maintained under stemness-promoting culture conditions. In addition, treatment resulted in the significant up-regulation of the previously absent expression of the pro-apoptotic proteins, p53 and p21 ("gene wake-up" effect), and as a result, a dramatic increase in sensitivity to treatment. In a patient-derived prostate CSC xenograft model, DHA-SBT-1214 was superior to ABRAXANE® and resulted in tumor clearance. This shows the long-term efficacy of DHA-SBT-1214 against drug resistant pancreatic, prostate and breast cancer tumors in vivo can be explained by its effects on both the bulk tumor and cancer stem cell sub-population.

In addition to evaluation of efficacy in CSC-rich PDAC models, the efficacy of NE-DHA-SBT-1214 in combination with antibody targeted to PD-L1 immune checkpoint inhibitor was examined in subcutaneous (subQ) Panc-2 syngeneic pancreatic cancer model developed in C56BL/6 mice. After transplantation of the Panc-2 cells, the mice were divided into groups for weekly treatment by intravenous administration of vehicle (as control), gemcitabine (at 120 mg/kg), ABRAXANE® (at 120 mg/kg) and NE-DHA-SBT-1214 (at 10 and 25 mg/kg) as either single in combination with either IgG control or anti-PD-L1 antibody (200 µg/dose). The antibodies were administered intraperitoneally. The treatment started two weeks after tumor transplantation when tumor mass became palpable at 50 to 150 mm$^3$ in volume.

Figure 4:
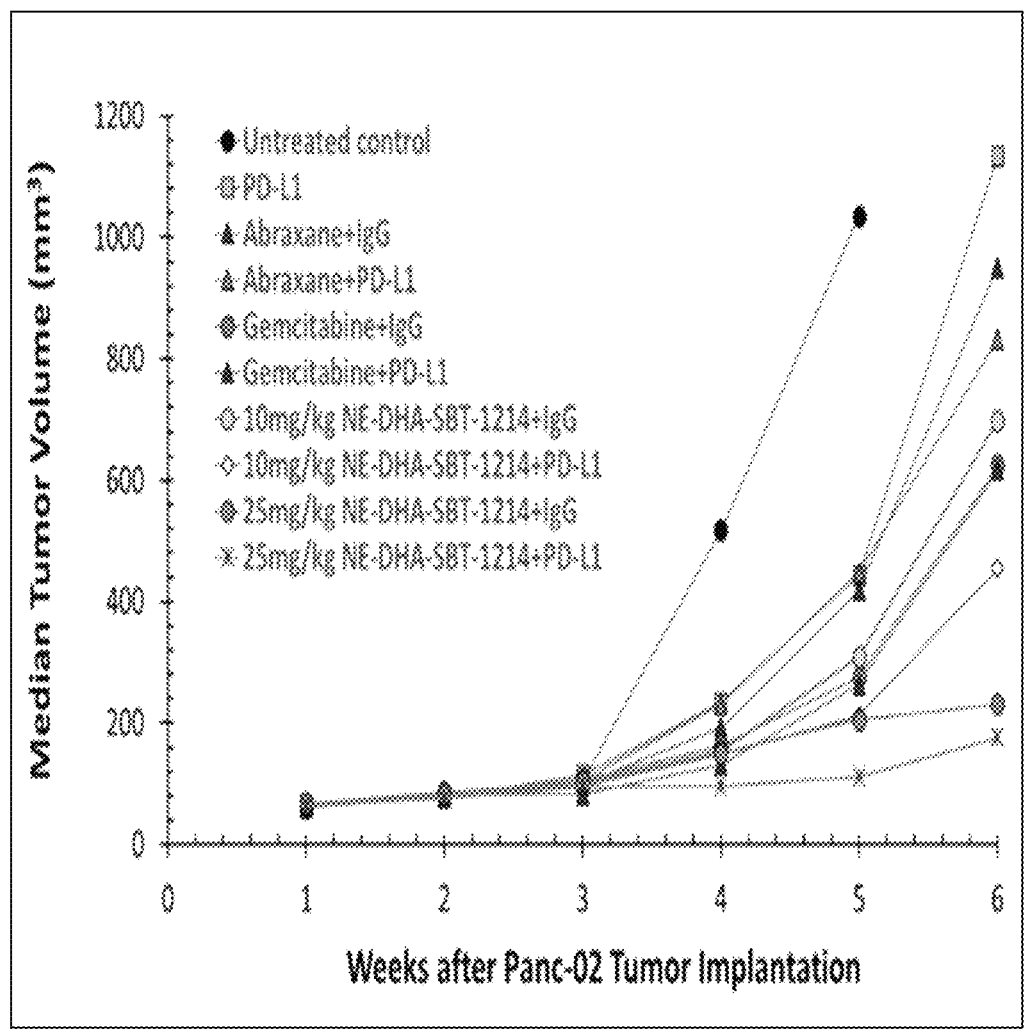
FIG. 4 is a graph of median tumor volume after Panc-02 tumor implant.

After 3 sets of weekly injections of the control and test formulations, the tumor volume changes were measured and the tumors were excised at the time of sacrifice. The results, presented in FIG. 4, show that the tumor growth suppression was significantly greater (p<0.05) for the NE-DHA-SBT-1214 group at 25 mg/kg and 10 mg/kg in combination with anti-PD-L1 antibody. In contrast to NE-DHA-SBT-1214, the optimal dose of ABRAXANE® (120 mg/kg) caused only insignificant suppression of the Panc-2-induced tumor and gemcitabine showed moderate effect. No significant body weight changes were induced by treatment with different drug combinations. All of the animals were sacrificed when the untreated control tumors reached a maximum dimeter of ~1 cm, as stated in the IACUC protocol. Upon sacrifice the tumor mass was excised and shows the smallest tumor mass from NE-DHA-SBT-1214 (25 mg/kg) and anti-PD-L1 antibody treatment group as compared to others.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Materials and Methods

Docosahexaenoic acid conjugate of SBT-1214 (i.e., DHA-SBT-1214) was synthesized by ChemMaster International, Inc. (Stony Brook, NY) following previously reported method. Extra pure grade omega-3 rich fish oil was purchased from JEdwards International (Quincy, MA), Lipoid E80 from Lipoid GMBH (Ludwigshafen, Germany), DSPE PEG2000 from Avanti Polar Lipids, Inc. (Alabaster, AL), Tween 80 from Sigma Chemicals, Inc. (St. Louis, MO), Dulbecco's Modified Eagle Medium (DMEM) and LAL chromogenic endotoxin quantitation kit from Thermo Scientific (Rockford, IL). Penicillin, streptomycin and Trypsin were obtained from Invitrogen (Grand Island, NY, USA). Female C57BL/6 mice (4-6 weeks old) were purchased from Charles River Laboratories (Frederick Research Model Facility-NCI) (Cambridge, MA, USA). Amicon Ultra-0.5 ml, Centrifugal filters from Millipore (Cork, Ireland). All other analytical grade reagents were purchased through Fisher Scientific. In the present study, we used Gemcitabine (GEM), paclitaxel (PTX) and ABRAXANE™ which are agents commonly used to treat pancreatic cancer; all agents were immediately prepared before use. GEM and PTX were purchased from Sigma Chemicals, Inc. (St. Louis, MO).

Preparation and Characterization of Nanoemulsion Formulations

Preparation of nanoemulsion formulations was carried out with a well-established protocol as reported recently with some modifications. Instead of a sonication method, oil-in-water nanoemulsions were prepared by high pressure homogenization method.

Cell Culture

The murine pancreatic cancer cell line Panc02, which is syngeneic to C57Bl/6 mice was a kind gift from Professor Michael A. Hollingsworth, UNMC, Omaha, NE. Panc02 cells were grown in 75 cm$^2$ cell culture flasks and maintained in DMEM medium supplemented with 10% fetal bovine serum (FBS), L-glutamine and penicillin (100 U/ml)/streptomycin (100 µg/ml) (both from Gibco Life Technologies, Carlsbad, CA, USA). Cells were incubated at 37° C. in a humidified atmosphere containing 5% $CO_2$.

In Vitro Evaluations of Nanoemulsion Uptake and Cellular Distribution

Panc02 cells ($0.5 \times 10^6$) were seeded onto glass cover-slips in 6-well plates for overnight at 37° C. in a humidified atmosphere containing 5% CO2. Then cells were incubated with 2 µM of NE-Rhodamine nanoparticles for different time points ranging from 0.5 hours to 4 hours to allow uptake of nanoparticles by cells. After last incubation time point, the glass cover-slips were washed with PBS before fixing in formalin for 15 minutes at room temperature. Nuclei of the fixed cells were stained with 4', 6-diamidino-2-phenylindole (DAPI). Uptake of rhodamine nanoemulsion was studied by a fluorescence confocal microscope (Zeiss LSM 700) with fixed parameters to have comparable uptake among different time points.

Cell Viability Studies

To see cytotoxic effect of different drugs and nanoemulsion formulation, 5000 cells were seeded in each well of the 96-well plate for overnight at 37° C. in a humidified atmosphere containing 5% CO2. Various drugs (Paclitaxel, Abraxane, Gemcitabine and solution and nanoemulsion of DHA-SBT-1214) were diluted at concentrations ranging from 0 nM, 0.01 nM, 0.1 nM, 1 nM, 10 nM, 100 nM, 1000 nM to 10000 nM and Panc02 cells treated with these concentrations for 96 hours. After incubation, cells were treated with 3-(4,5-dimethylthiazol-2-yl)-2,5-diphenyltetrazolium bromide (MTT). MTT crystals were dissolved with DMSO and plates were read at 570 nm absorbance using a BioTek Synergy HTX Multi-Mode Microplate Reader.

Expression of PD-L1 After Exposure to Different Therapeutic Agents

Cells were seeded at $0.5 \times 10^6$ cells/well in 6-well plates for overnight at 37° C. in a humidified atmosphere containing 5% CO2. After 24 hours, cells were exposed to $IC_{50}$ value of different drugs as mentioned in FIGS. 5A and 5B for 48 hours. The percentage maximal response is shown as a function of anti-cancer agents when administered to Panc02 cells. The cell viability was measured by the MTT assay after 96 hours of incubation at 37° C. Data represent mean±standard deviation (n=3). Significant differences are indicated as follows: *p<0.05, and **p<0.01. The expression level of PD-L1 was determined using flow cytometry as follows. Briefly, cells harvested from in vitro cultures were washed twice with 3% BSA/PBS and then incubated with rat anti-PD-L1 or isotype control antibodies (mouse, BioXcell, West Lebanon, NH, USA) for 30 minutes at 4° C., then washed three times and incubated with anti-rat AlexaFluor 488 conjugated Antibody. The cells were washed once with 3% BSA/PBS and analyzed by flow cytometer on a FACSCalibur flow cytometer and CellQuest™ Pro version 6.0 software (both from Becton-Dickinson and Co.).

Immunoblotting

Cells and tumor tissues were washed twice with phosphate-buffered saline (PBS) and lysed in ice-cold lysis buffer containing 2% proteinase inhibitor (both from Sigma-Aldrich Co., St. Louis, MO, USA). Cells were retrieved with a cell scraper, stirred and incubated on ice for 15 minutes. Mice tumor tissues were sonicated for 10 seconds on ice with sonicator. Lysates were centrifuged, supernatants were collected, and protein concentration was determined using the Bio-Rad protein assay (Bio-Rad Laboratories, Hercules, CA, USA). The supernatants were diluted with lysis buffer to create equal concentrations of protein. Fifty micrograms of protein were separated on 4-12% Bis-Tris gels and transferred onto a nitrocellulose membrane using the iBlot Dry Blotting System (all from Life Technologies) according to the manufacturer's protocol. Blots were blocked with 1% dry milk in TBS-T [10 mM Tris-HCl (pH 8.0), 150 mM NaCl, 0.1% Tween-20 v/v] for 1 hour at room temperature and washed once with TBS-T. The membranes were incubated overnight at 4° C. with anti-PD-L1 (from Abcam), PD-1, F4/80 and Histone 3 (all from Cell Signaling Technology, Inc.) antibodies in TBS-T (diluted 1:1,000). After washing in TBS-T three times, the membranes were incubated with the secondary anti-rabbit and mouse IgG antibodies (Life Technologies) in TBS-T (diluted 1:10,000) for 1 hour at room temperature. Immunocomplexes were detected using western blotting (ECL Prime; GE Healthcare UK Ltd., Buckinghamshire, UK).

Real Time-Polymerase Chain Reaction (RT-PCR)

The expression level of PD-L1 and mRNA for other proteins was determined using real-time PCR as previously described. The samples used for mRNA isolation were removed from the pancreatic cancer cells (Pan02) or tumor tissues. Total mRNA was extracted using commercially available RNA extraction kit according to mentioned protocol (Thermo Fisher Scientific (Rockford, IL). The isolated RNA was stored at −80° C. until use for real-time PCR. In the latter, 1 μg of extracted RNA was reverse-transcribed using commercial cDNA synthesis kit (Thermo Fisher Scientific (Rockford, IL). The resulting cDNA was subjected to RT-PCR with Applied Biosystems™ PowerUp™ SYBR™ Green Master Mix (Thermo Fisher Scientific (Rockford, IL), using the following primers for mouse PD-L1: (forward primer, 5'-AAAGTCAATGCCCCATACCG-3' (SEQ ID NO: 1) and reverse primer, 5'-TTCTCTTCCCACT-CACGGGT-3' (SEQ ID NO: 2)); mouse PD-1 (forward primer, 5'-TTCACCTGCAGCTTGTCCAA-3' (SEQ ID NO:4) and reverse primer, 5'-TGGGCAGCTGTAT-GATCTGG-3' (SEQ ID NO: 5)); CD4: (forward primer, 5'-ACACACCTGTGCAAGAAGCA-3' (SEQ ID NO:6) and reverse primer, 5'-GCTCTTGTTGGTTGGGAATC-3' (SEQ ID NO: 7)); mouse CD8 (forward primer, 5'-CT-CACCTGTGCACCCTACC-3' (SEQ ID NO: 8) and reverse primer, 5'-ATCCGGTCCCCTTCACTG-3' (SEQ ID NO:9)); mouse Arginase-1 (forward primer, 5'-GAACACGGCAGTGGCTTTAAC-3' (SEQ ID NO: 10) and reverse primer, 5'-TGCTTAGCTCTGTCTGCTTTGC-3' (SEQ ID NO: 11)); and mouse R-actin (forward primer, 5'-CTCCTGAGCGCAAGTACTCTGTG-3' (SEQ ID NO: 12) and reverse primer, 5'-TAAAACGCAGCTCAGTAACAGTCC-3' (SEQ ID NO: 13)). PCR was performed using a real-time PCR system (7300; Applied Biosystems, Foster City, CA, USA). Relative quantifications of gene expression with qRT-PCR data were calculated relative to murine β-actin.

In Vivo Studies—Subcutaneous Tumor Induction and Growth

All experiments involving the use of animals were carried out in strict accordance with the recommendations in the guide for the care and use of laboratory animals of the National Institutes of Health, via a research protocol that was approved by Northeastern University Institutional Animal Care and Use Committee (IACUC). Briefly, after sufficient propagation, Panc02 murine pancreatic cancer cells were resuspended in 1:1 PBS/Matrigel and $2 \times 10^5$ cells injected subcutaneously to the right flanks of a 6 weeks old C57Bl/6 mice. Tumor development was monitored twice weekly. The tumor size was measured with a caliper on a weekly basis and approximate tumor volumes determined using the formula $0.5ab^2$, where b is the smaller of the two perpendicular diameters. The mice were killed when tumor size reached ≥1500 mm² in diameter.

In Vivo Single and Combination Therapies

Mouse Antibody against PD-L1 (10F.9G2) and relevant isotype IgG control was purchased from Bio X Cell. Two hundred micrograms of antibody against PD-L1 and relevant isotype IgG control was injected through IP per mice twice a week for 3 weeks. Gemcitabine solution and abraxane 120 mg/kg was injected through i.p. once a week. Paclitaxel 120 mg/kg and NE-DHA-SBT-1214 either 10 mg/kg or 25 mg/kg was injected once a week through i.v. All chemotherapy drugs were either injected in combination to anti PD-L1 antibody or isotype IgG control. In total, three treatments were given per experiment.

Histology and Immunohistochemistry (IHC) Analysis of Tumor Tissues

Histological analysis of tumor burden in mice was done on formaldehyde-fixed and paraffin-embedded tumor tissues using hematoxylin and eosin (H&E) staining. IHC was done on paraffin-embedded tissue sections for PD-1, CD4 and CD8 antibodies. All mouse specific antibodies against PD-1, CD4 and CD8 were purchased from cell signaling technology. IHC was processed according to the protocol and recommended dilution from cell signaling technology.

Statistical Analysis

All results are expressed as the means±SD. For therapeutic experiments, three mice were assigned per treatment group. Statistical analysis was performed with GraphPad Prism 6 software. Data were analyzed using unpaired Student's t test, and ANOVA and its differences were considered to be significant at $p<0.05$.

Results

Characterization of DHA-SBT-1214 Nanoemulsion Formulation

Figure 6A:
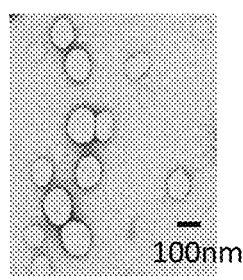
FIG. 6A is a transmission electron microscopy (TEM) of nanoemulsion.
Figure 6B:
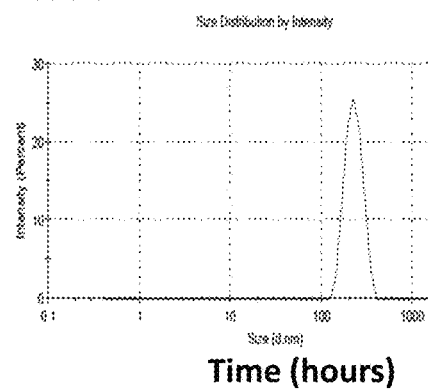
FIG. 6B shows the oil droplet particle size determination in nm.
Figure 6C:
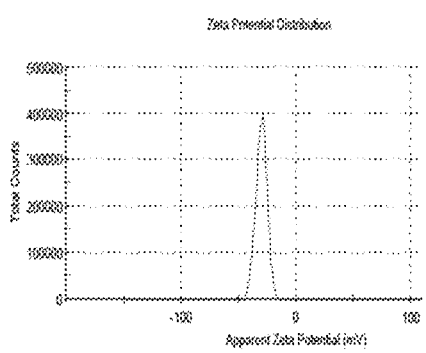
FIG. 6C shows the measurement of zeta potential or surface charge on the oil droplets in mV.

Nanoemulsion delivery approach has shown enhanced therapeutic potential in Applicants' previous studies. In this study, Applicants have formulated an oil-in-water nanoemulsion of DHA-SBT-1214, a new-generation taxoid using fish oil which is rich in PUFAs such as omega-3 and omega-6 fatty acids. This taxoid encapsulated nanoemulsion was used to study its therapeutic efficacy in combination with immune check point inhibitor in a pancreatic cancer preclinical mouse model. Applicants have used a high pressure homogenization technique to formulate this uniform, milky-white and stable nanoemulsion. As shown in FIGS. 6A-6D, the nanoemulsion droplets were near spherical in morphology with an average diameter of approximately 220 nm, as observed by light scattering and transmission electron microscopy (TEM). Fluorescence microscopy images showing the blue (nucleus), red (rhodamine encapsulated nanoemulsion) and overlay images in purple color. The images were taken at 63× magnification. The image scale bar is 100 μm. Along with particle size, uniformity and charge of the nanoemulsions also predicts their bioavailability. Uniformity is represented by polydispersity index (PDI) and the lower value of PDI (<0.2) indicates uniform and stable form of nanoemulsions. PDI values of drug encapsulated nanoemulsions were less than 0.1. The average surface charge of the oil droplets in the nanoemulsions was −28.9 mV (FIG. 6C). The negative charge of the nanoemulsion could be due to the presence of free fatty acids of the fish oil used in the preparation of these nanoemulsions.

An HPLC assay was used to determine the drug concentrations in the nanoemulsion formulations. DHA-SBT-1214 nanoemulsion at 20 mg/ml represents drug loading efficiency of 97%. This high drug encapsulation efficiency of nanoemulsions was attributed to the relative lipophilicity of the drug, as this drug was retained in the oil core of the nanoemulsion. All the formulations were filtered through 0.2-micron filter and had a minimum level of endotoxin as confirmed through Limulus Amebocyte Lysate (LAL) assay during the storage period.

In Vitro Evaluations of DHA-SBT-1214 Formulations in Panc02 Cells

Figure 6D:
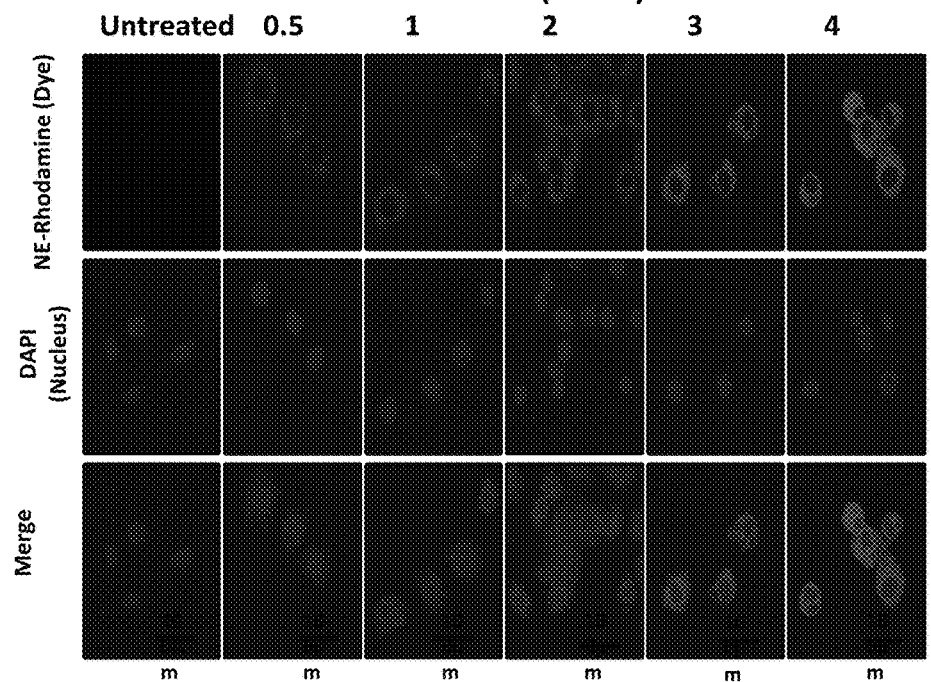
FIG. 6D shows the uptake of rhodamine-encapsulated nanoemulsion formulation in Panc02 cells.

To examine whether nanoemulsions were internalized in Panc02 cells, rhodamine was encapsulated into nanoemulsions and confocal microscopy studies were performed. The optimal cell and spheroid uptake of rhodamine encapsulated nanoemulsion formulation was observed after rhodamine 2 μM incubation at different time points (FIG. 6D). As shown in FIG. 6D, the images clearly depict that the nanoemulsions do efficiently deliver the encapsulated dye in the cells and that the increased fluorescence signal at increased time points of rhodamine nanoemulsion treated cells indicates the higher intracellular uptake by Panc02 cells. Since the internalization of nanoemulsion formulation was confirmed by cell uptake experiments, we replaced rhodamine with DHA-SBT-1214 in the nanoemulsion formulation and compared its effect on cell viability with different anti-cancer drugs.

The cell-kill efficiency of different anti-cancer drugs was examined in Panc02 cells using the MTT assay. In addition to blank nanoemulsion or vehicle control, the final concentrations of DHA-SBT-1214 selected for these studies were 0.01 nM, 0.1 nM, 1 nM, 10 nM, 100 nM, 1,000 nM to 10,000 nM based on previous studies of SBT-1214 [6]. The concentration-response studies against DHA-SBT-1214 and other anticancer agents in Panc02 cells are shown in FIGS. 5A-5B. The results are shown as percent viable cells remaining as a function of treatment following 96 hours of drug exposure at 37° C. When DHA-SBT-1214 was administered at 10 and 100 nM concentrations, higher cytotoxicity was observed with the nanoemulsion formulation as compared to the aqueous solution. However, under in vitro conditions, gemcitabine showed highest potency with average $IC_{50}$ value of 154 nM, followed by 215 nM for DHA-SBT-1214 nanoemulsion and 262 nM for DHA-SBT-1214 in solution. In contrast, the average $IC_{50\ values}$ of paclitaxel and Abraxane™ were significantly higher at 443 nM and 428 nM, respectively.

Evaluation of PD-L1 Expression Following Drug Therapy in Panc02 Cells

Figure 7:
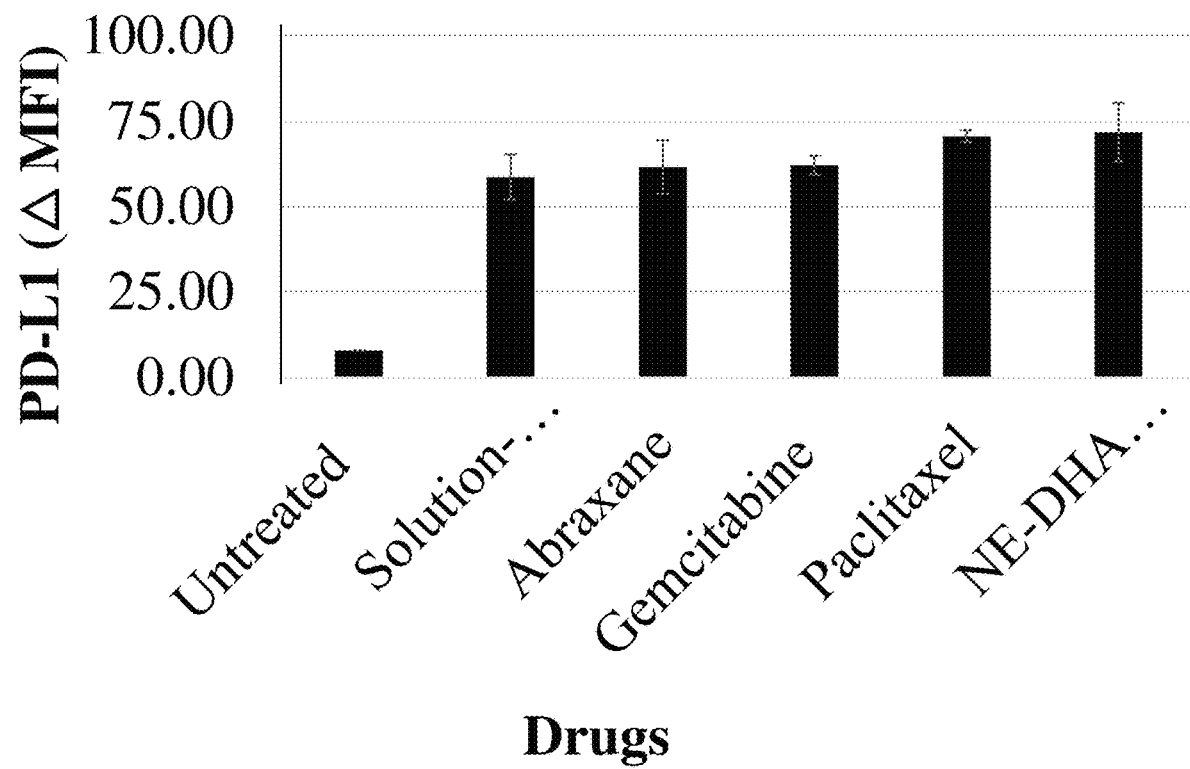
FIG. 7 is a graph of PD-L1 surface protein expression in response to different anti-cancer agent treatments in vitro and without any treatment in vivo.
Figure 8:
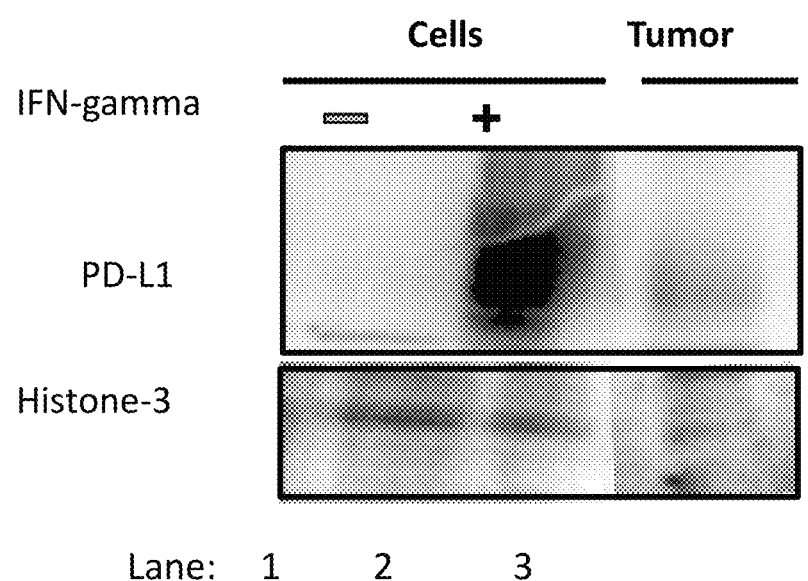
FIG. 8 is a Western blot of untreated and IFN-gamma (20 ng/ml for 4 h) treated Panc02 cells compared to Panc02 mouse tumor.

Panc02 cells were treated with gemcitabine, Abraxane™, paclitaxel and DHA-SBT-1214 both in solution and nanoemulsion for 48 hours to determine whether they can induce PD-L1 protein expression. PD-L1 expression levels on tumor cells were determined by flow cytometry and is expressed as the A mean fluorescence intensity ($\Delta$MFI; MFI using anti-PD-L1 subtracted from the isotype control). As shown in FIG. 7, treatment with different anticancer drugs at their $IC_{50}$ values for 48 hours induced PD-L1 surface expression in Panc02 murine pancreatic cancer cells. PD-L1 upregulation in response to the anticancer agents tested was significantly increased compared to the untreated control. PD-L1 expression was analyzed using flow cytometry and is presented as $\Delta$MFI (MFI using anti-PD-L1 subtracted from the isotype control). Data represent the mean±standard deviation of at least 3 independent experiments; *p<0.05, p<0.01, *p<0.001. As reported previously, PD-L1 level enhanced in pancreatic tumor tissues compared to in vitro growing cells as shown in FIG. 8.

In Vivo Evaluation of Combination Drug and Anti-PD-L1 Antibody Therapy

Figure 9:
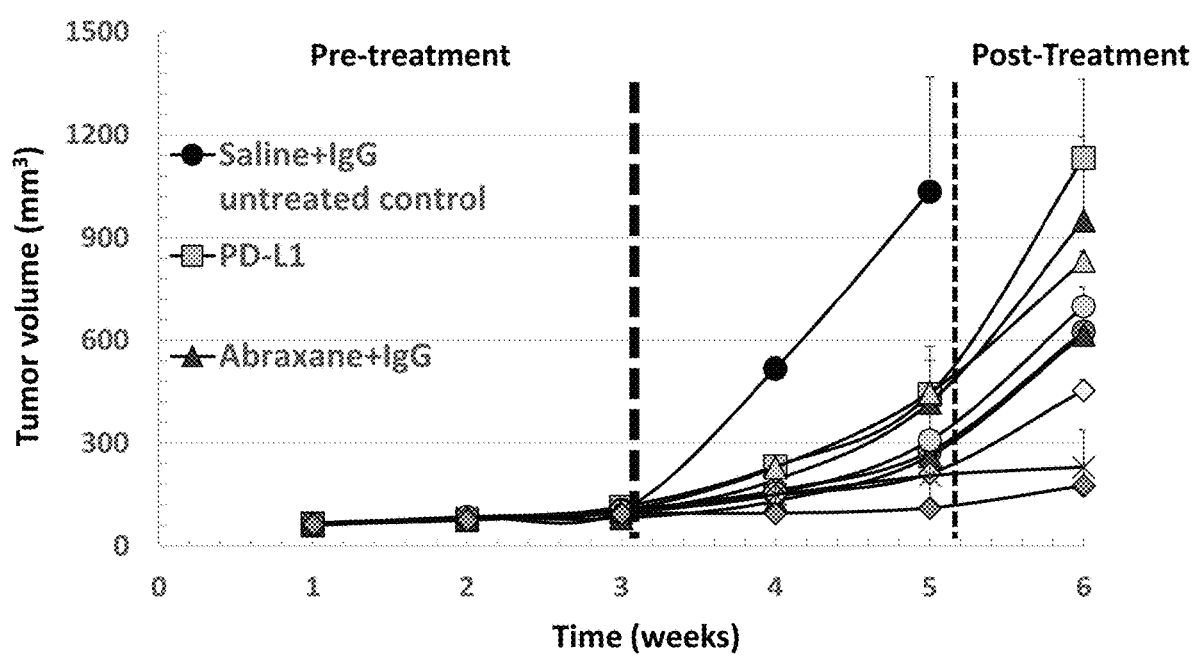
FIG. 9 is a graph of tumor volume versus time for treatments tested.
Figure 10:
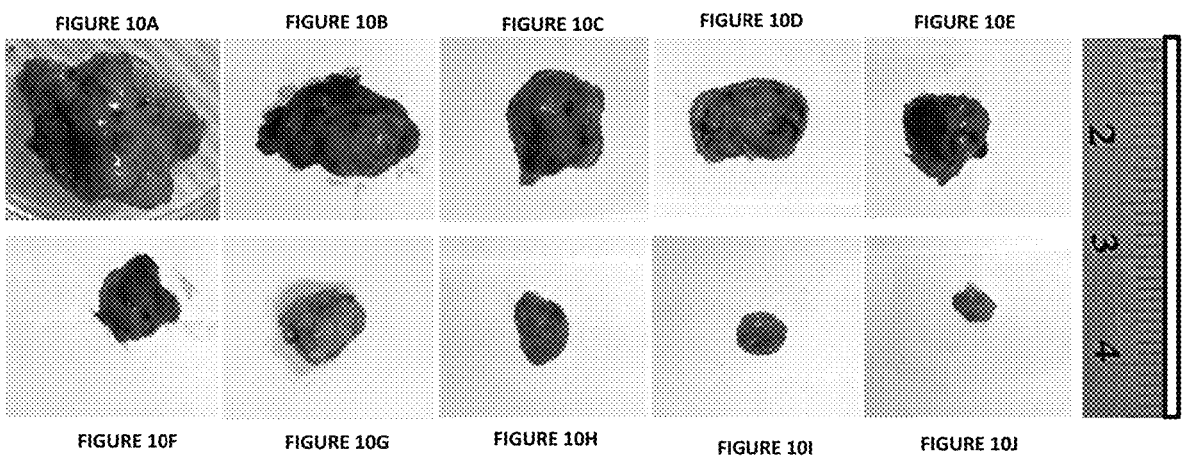
FIGS. 10A-10J are tumor images taken at the time of harvest from different treatment modalities.
Figure 11:
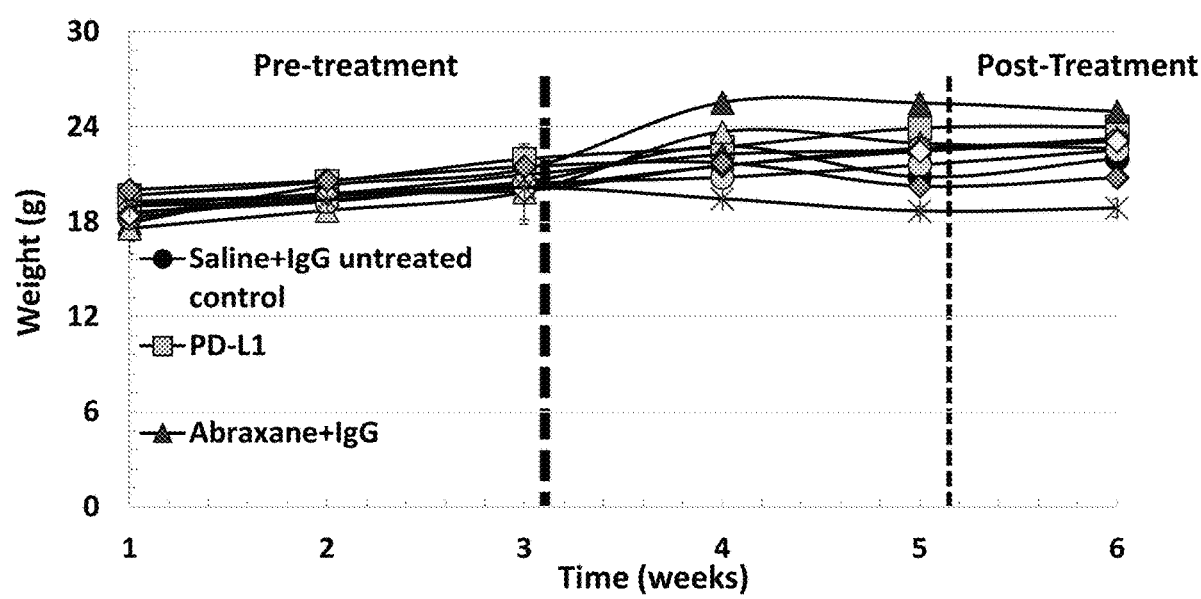
FIG. 11 is a graph showing body weight alterations induced by treatment with different combination therapies.

Applicants have examined the effect of different anticancer agents either alone or in combination to blocking antibody against PD-L1 on Panc02 induced tumor growth in vivo. Panc02 cells were directly injected into subcutaneously and tumor volumes were measured one week later and continued till the end of the experiment. After tumor size reaches approximately 100 mm$^3$, Applicants randomized the mice to have approximately equal tumor volume among all treatment groups. Then, mice were treated with either anticancer agents either alone or in combination to PD-L1 antibody for three weeks. FIG. 9 and FIGS. 10A-10J, show the tumor growth inhibitory effects of each treatment group after the three week-treatment. FIG. 9 is a graph summarizing all treatment modalities. The values are means±SD (n=3). Significant differences are indicated as follows: *p<0.05, and **p<0.01. As compared with the untreated control group, each treatment group had inhibitory effect which was most prominent in 25 mg/kg NE-DHA-SBT-1214 in both IgG and antibody combination treated groups. These results indicate that blocking of only PD-L1 was not efficient in reducing tumor growth but in combination with 25 mg/kg NE-DHA-SBT-1214 significantly inhibited tumor growth. NE-DHA-SBT-1214 treatment even at 10 mg/kg in combination to PD-L1 antibody was more effective in suppressing tumor growth compared to standard chemotherapy drug, gemcitabine. Treatment with 10 mg/kg DHA-SBT-1214 was superior to abraxane treatment at 120 mg/kg. Overall, a combinational treatment of NE-DHA-SBT-1214 with anti-PD-L1 antibody showed a synergistic effect compared with single treatment. As a crude proxy for toxicity there was no significant weight change within each treatment group as shown in FIG. 11.

Anticancer Drugs Induce PD-L1 Expression In Vivo in Panc02 Tumor Model

Figure 12:
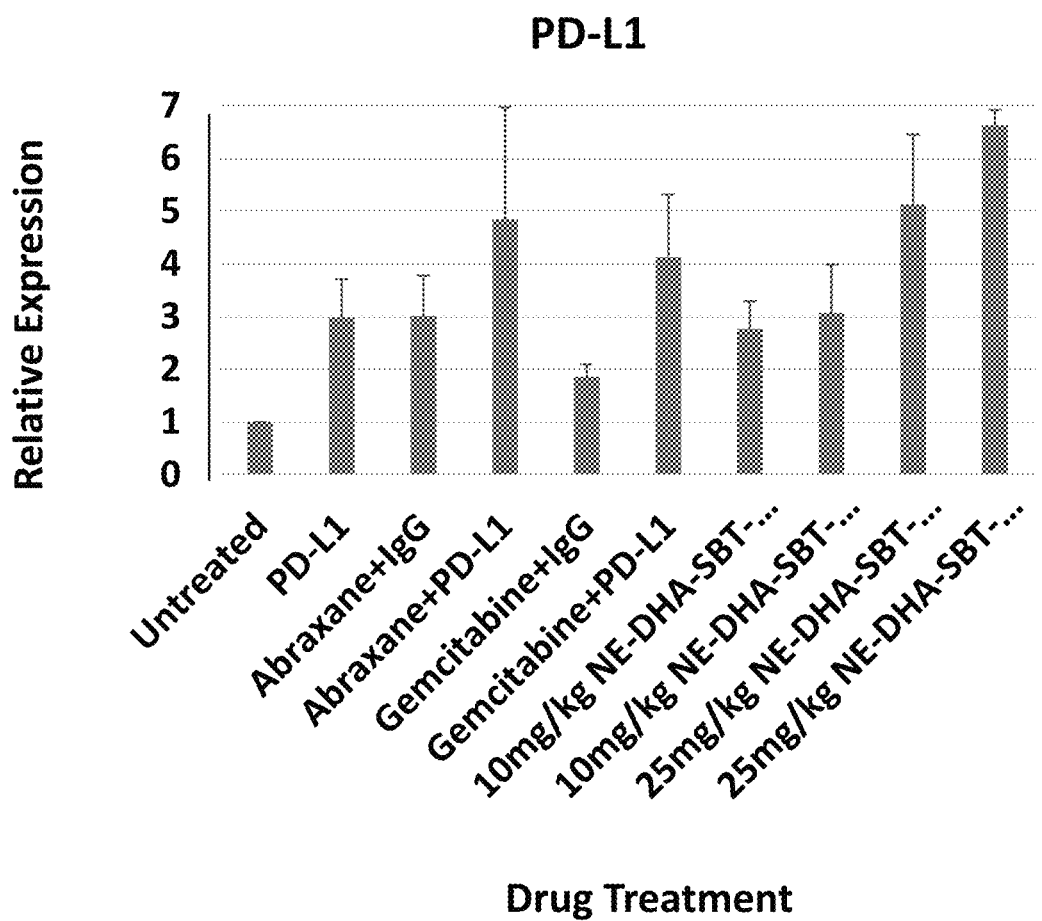
FIG. 12 is a graph of mRNA expression of PD-L1 from different mouse tumor treatment groups analyzed using RT-PCR and relative gene expression for RT-PCR data was calculated relative to murine β-actin.
Figure 13:
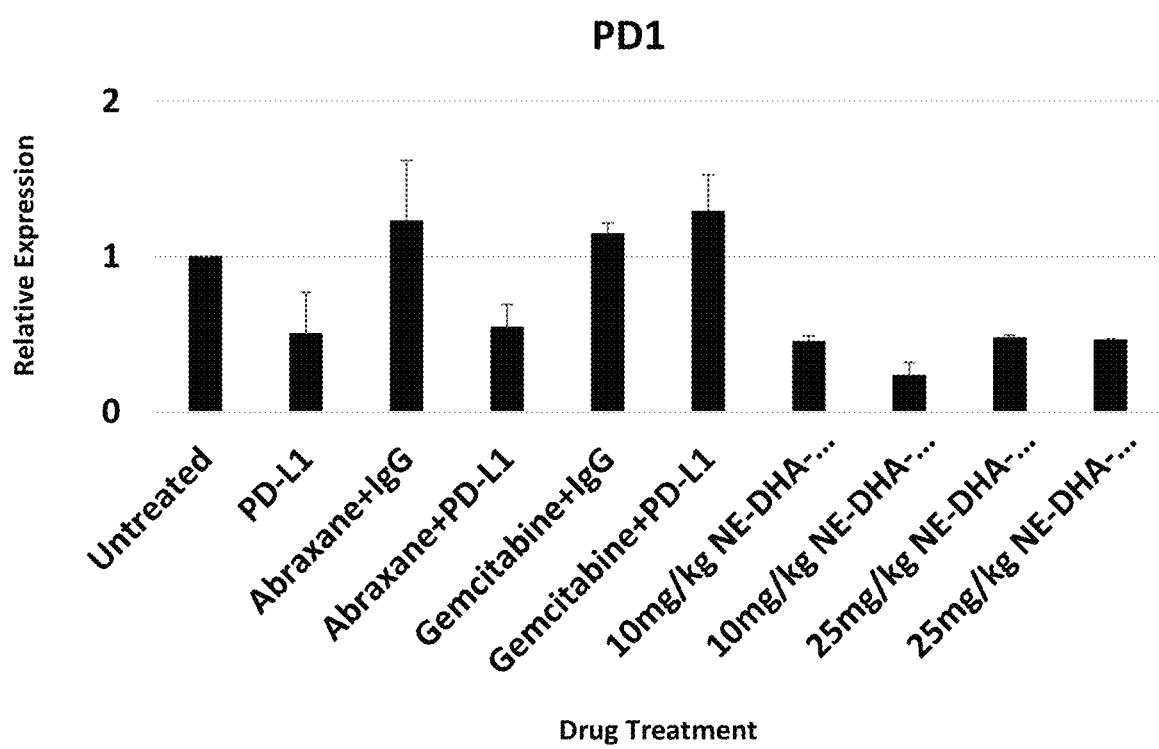
FIG. 13 is a graph of mRNA expression of PD-1 from different mouse tumor treatment groups analyzed using RT-PCR and relative gene expression for RT-PCR data was calculated relative to murine β-actin.
Figure 14:
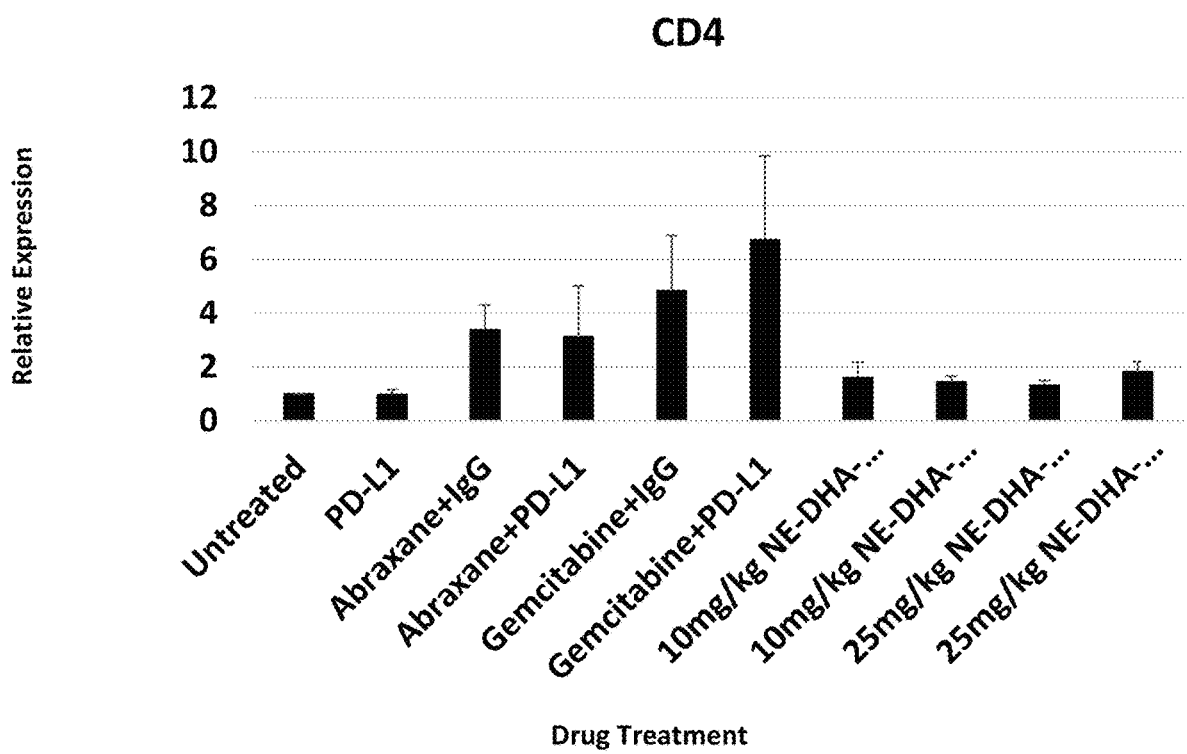
FIG. 14 is a graph of mRNA expression of CD-4 from different mouse tumor treatment groups analyzed using RT-PCR and relative gene expression for RT-PCR data was calculated relative to murine β-actin.
Figure 15:
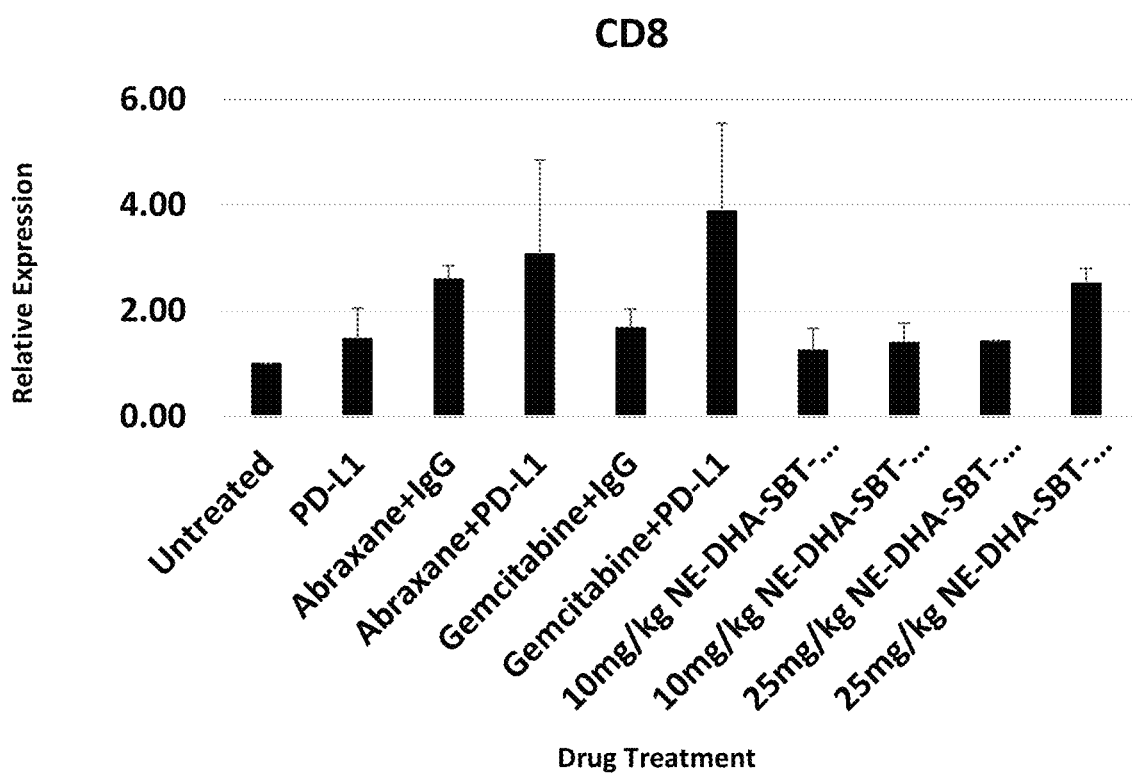
FIG. 15 is a graph of mRNA expression of CD-8 from different mouse tumor treatment groups analyzed using RT-PCR and relative gene expression for RT-PCR data was calculated relative to murine β-actin.
Figure 16:
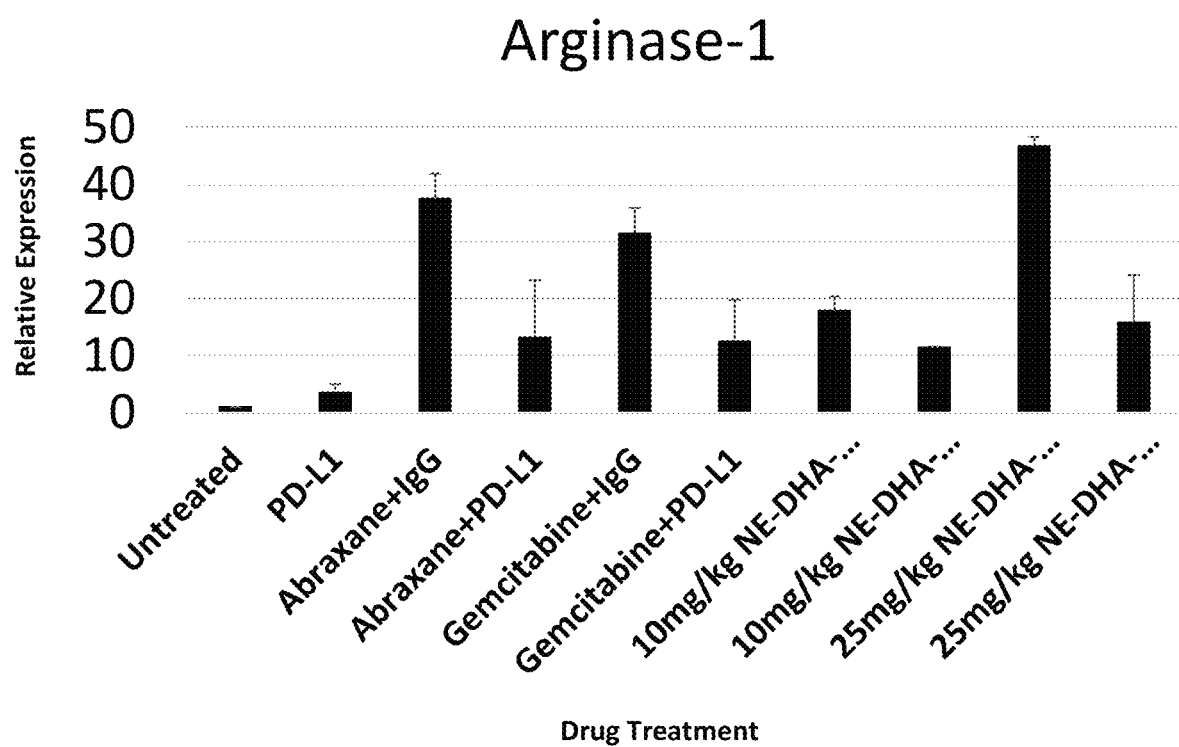
FIG. 16 is a graph of mRNA expression of Arginase-1 from different mouse tumor treatment groups analyzed using RT-PCR and relative gene expression for RT-PCR data was calculated relative to murine β-actin.

To investigate how the anticancer agents, induce PD-L1, PD-1, CD4, CD8 and Arginase-1 mRNA expression in pancreatic cancer tumor tissues, the mRNA level of PD-L1, PD-1, CD4, CD8, and Arginase-1 either alone or in combination of immune checkpoint inhibitor was determined by RT-PCR. PD-L1 mRNA level was upregulated in combination therapy among all the anticancer agents compared to their respective IgG control groups as shown in FIG. 12. However, PD-1 and CD4 mRNA level was lower in anti-PD-L1 plus anticancer agents except gemcitabine which was not significantly higher compared to its IgG treated group as shown in FIGS. 13 and 14, respectively. CD8 mRNA level was upregulated in response to combination treatment of all anticancer agents when combined with immune check point inhibitor compared to their IgG treated groups as shown in FIG. 15, respectively. However, Arginase-1 level was significantly higher in IgG treatment group compared to their immune check point inhibitor as described in FIG. 16. In addition to upregulation of PD-L1 mRNA expression level, treatment of anticancer agents in combination to immune check point inhibitor also enhance PD-L1 protein expression level as shown in FIG. 17. Data represent the mean±standard deviation of at least 3 independent experiments; *p<0.05, p<0.01. Similar to PD-L1 protein expression, PD-1 expression was also up-regulated except higher dose of NE-DHA-SBT-1214 compared to its IgG treatment group. Higher PD-L1 protein level might be attributed to presence of macrophages in this higher dose NE-DHA-SBT-1214 treated group, which is evident due to higher protein level of F4/80 in FIG. 17**.

Infiltration of CD4+, CD8+, and PD-1 Cells in Panc02 Tumor

Applicants then examined the infiltration of CD4+, CD8+, and PD-1 cells in tumor tissues on day 21 by histology (FIGS. 18A-18J) and by immunohistochemistry (FIGS. 19A-19J, 20A-20J, and 21A-21J). The tumor tissue histology from different treatment groups showed that tumor from NE-DHA-SBT-1214 treated group has less dense stroma compared to solid tumor mass from other treatment groups (FIGS. 18A-18J). The images were taken at 63× magnification.

In untreated control tumor tissues, a relatively small number of CD4+ cells were found. As compared to the untreated tumors, infiltration of CD4+ cells was significantly increased by anti-PD-L1 treatment and with different anticancer agents combination treatments (FIGS. 19A-19J).

Only a small number of CD8+ cell infiltrations were observed in control tumor tissue. Treatment with anti-PD-L1 antibody in combination with NE-DHA-SBT-1214 resulted in a significant increase of CD8+ cell infiltration in tumor microenvironment (FIGS. 20A-20J). The infiltration of CD8+ cells in the core of pancreatic tumor is probably responsible for the suppression of tumor growth in each of the different treatment groups. However, expression of PD-1 on the T-cells was comparable among all treatment groups (FIGS. 21A-21J).

Discussion

Pancreatic cancer remains an intractable disease due to development of resistance to conventional anticancer agents. Currently, there is a great of enthusiasm around the potential for immunotherapy in many treatment regimens due to the success of immune checkpoint inhibitors and new generations of adoptive cell transfer therapy, such as chimeric antigen receptor (CAR) T cell therapy. However, immune checkpoint inhibitors have not shown promising results when used as a single treatment regimen in many tumor types, especially in certain solid tumors, such as PDAC. As such, there is extensive effort toward effectively combining immune- and non-immune based cancer therapies with the aim of improving response rate and efficacy.

For PDAC patients, gemcitabine is being used as frontline treatment in combination with ABRAXANE™; however, the survival benefit is minimal. Paclitaxel is still a front-line treatment for many solid tumor types, it initiates the apoptosis and causes cell cycle arrest at the G2/M stage. Taxanes, particularly paclitaxel in Cremophor-ethanol formulation (TAXOL®), have some toxicity issues due to its delivery vehicle and lack of tumor specific delivery. To further improve the efficiency of paclitaxel, numerous formulations as well as prodrugs of paclitaxel have been developed that increase its aqueous solubility, such as cyclodextrin, liposomes and albumin-bound nanoparticle (ABRAXANE™) formulations. However, some cancers including colon and prostate overexpress P-glycoprotein (Pgp), an effective ATP-binding cassette (ABC) transporter and effluxes paclitaxel, that is why paclitaxel is not effective against these cancers. In order to overcome efflux issue, Paclitaxel was conjugated with DHA, because DHA conjugated drug has higher affinity for human serum albumin which is the primary carrier for PUFAs in the bloodstream, but in cancers which overexpress Pgp and/or other ABC transporters, when paclitaxel free itself from DHA in the presence of esterase, even though it will be released slowly but still be caught by the efflux pump(s) and eliminated from the cancer cells.

In contrast to paclitaxel, a new-generation taxoid, named SBT-1214, had showed excellent activity against drug-resistant cancer cells, which express MDR phenotypes. In previous studies, DHA-conjugated SBT-1214 improved therapeutic efficacy by increased accumulation of drug at the tumor site through the EPR effect. To further improve the efficacy of DHA-SBT-1214, Applicants successfully formulated and studied the nanoemulsion carrier system containing DHA-SBT-1214 in fish oil droplets, which favorably acted as drug reservoir. This colloidal system has desired particle size and zeta potential to preserve the stability of formulation in vitro and enhance its performance in vivo. The surface morphology DHA-SBT-1214 nanoemulsion formulation was spherical in morphology with no visible drug crystals. The qualitative cellular uptake analysis demonstrated that the nanoemulsion formulations were efficiently internalized in Panc02 cells. This suggests that the nanoemulsions did efficiently deliver the payload to the subcellular sites in the cell and was more potent than its drug solution. In our recent study, Applicants observed that DHA-SBT-1214 suppressed tumor growth to a higher extent when delivered in nanoemulsion formulations emphasizing its higher therapeutic efficacy when used as stand-alone therapy. In conclusion, Applicants' data from that study demonstrated that nanoemulsion of the DHA-SBT-1214 conjugate induces superior regression and tumor growth inhibition and has high potential as a novel anti-cancer drug candidate.

In the current study, Applicants explored the efficacy of the combination of immune therapy and anticancer agents in pancreatic cancer. As reported previously, PD-L1 surface expression in pancreatic cancer cell lines Panc02 was upregulated by paclitaxel, ABRAXANE™ DHA-SBT-1214 and gemcitabine.

To the best of Applicants' knowledge, this is the first study to address the effect of anticancer agents in combination to check point inhibitor on PD-L1 expression in a syngeneic pancreatic cancer mouse model. Although the effect of chemotherapy agents on PD-L1 expression has been discussed in previous studies, there have been conflicting findings. For instance, three studies demonstrated that anticancer agents upregulated surface PD-L1 expression, while one study reported the downregulation of surface PD-L1. For example, Gong, et al. reported that paclitaxel induced PD-L1 surface protein and mRNA expression in two different cancer cell models. Similarly, Peng reported that PD-L1 expression in ovarian cancer cell lines was augmented via NF-κB signaling by paclitaxel, gemcitabine or carboplatin treatment. In contrast, Ghebeh, et al. reported that doxorubicin downregulated the surface expression of PD-L1 in breast cancer cells and upregulated nuclear expression of PD-L1. One possible explanation for the difference among these previous studies, might be due to differences in the cell lines and anticancer agents used in each study.

In the present study, Applicants used ABRAXANE™, gemcitabine, paclitaxel as well as both solution and nanoemulsion formulation of DHA-SBT-1214, used alone or combined with other agents when treating pancreatic cancer. The concentration of each anticancer agent in our experiments was based on $IC_{50}$ value of Panc02 cells. The respective difference in drug concentration among the anticancer agents have not significantly influenced the degree of PD-L1 induction by the agents and the PD-L1 surface protein expression was enhanced in response to all anticancer agents as determined by flow cytometry. In regards to the mechanism of PD-L1 regulation, Pardoll reported that innate and adaptive immune resistance are the two general mechanisms by which tumor cells regulate PD-L1. In general, anticancer agents not only cause cytotoxicity, but also alter the tumor immune response, which may induce tumor immune escape. In this study, Applicants demonstrated anti-tumor effects of different anticancer agents in combination to PD-L1 blockade in vivo by using a syngeneic murine pancreas cancer model. It is well known that PD-1/PD-L1 interactions induce a negative regulation, which is critical for immune homeostasis after activation of T cells. This negative regulation is thought to be beneficial for cancer cells to escape from tumor-specific T-cell immunity. There has also been a study using a pancreas cancer cell line that showed PD-L1 blocking inhibited tumor development, although these studies have not used anticancer agents along with immune check point inhibitor. Applicants used a pancreas cancer model established by subcutaneous injection of murine pancreatic cancer cells into the mouse pancreas because cancer immunity is highly regulated by specie-specific leukocyte recruitment. As a result, blocking of PD-L1 reduced rate of tumor growth in our pancreas cancer model when used as a single treatment option or when used in combination with commonly used anticancer agents (Paclitaxel, Abraxane and Gemcitabine) for pancreatic cancer. However, combination of NE-DHA-SBT-1214 with PD-L1 blockade showed significant tumor suppression and kept tumors regressed even after treatment, showing that PD-L1 is a possible target for treatment of pancreas cancer.

Freeman, et al. reported that PD-L1 reduced T-cell proliferation, however, Applicants found that the number of tumor-infiltrating cells was increased after anti-PD-L1 antibody treatment. Increase in IFN-gamma by blocking of the PD-1/PD-L1 pathway has been demonstrated in several models, including chronic infectious diseases, in addition to cancer immunity. Treatment with anti-PD-L1 antibody increased the expression of PD-L1 that might be due to increased infiltration of IFN-gamma producing CD8+ cells to tumor tissue. Another possible reason for upregulation of PD-L1 mRNA and protein level after anti-PD-L1 antibody treatment is the recruitment of macrophages and myeloid derived suppressor cells (MDSC) which also express PD-L1. The increased IFN-gamma from infiltrating CD8+ cells in tumor tissue might contribute to the antitumor effect, because a large amount of IFN-gamma expression from effector T cells for a long period can induce infiltration of inflammatory cells such as M1 macrophages which enhance anti-tumor immunity. Macrophages in tumor microenvironment overexpress Arginase-1 indicating that these macrophages are M1 in addition to possible presence of MDSC. Thus, it is conceivable that the suppressive effect of anti-PD-L1 antibody on tumor growth can be mainly explained by the increased number of tumor-infiltrating effector cells in NE-DHA-SBT-1214 combination treatment group. In other words, in the untreated group, PD-L1 might attenuate tumor immunity in this cancer model by decreasing the infiltration of IFN-gamma-producing T cells and M1 macrophages. The same cells that were injected into mice to form a pancreatic tumor expressed very high levels of PD-L1 after IFN-gamma treatment in vitro. In Applicants' study, the number of tumor-infiltrating CD4+ T cells did not decrease after PD-L1 blockade. Taken together, the results show that PD-L1 blockade can decrease the pancreatic tumor burden through synergistic effects of NE-DHA-SBT-1214. Furthermore, histology of tumor tissues from different treatment groups showed that tumors from the NE-DHA-SBT-1214 treated group has less dense stroma compared to the solid tumor mass from other treatment groups. However, the single therapy and the combination therapy of most commonly used anticancer agents unexpectedly did not show an additive anti-tumor effect except NE-DHA-SBT-1214. One possible explanation for better efficacy of NE-DHA-SBT-1214 is its role in treating cancer stem cells as compared to other anti-cancer agents.

CONCLUSIONS

In summary, Applicants' results indicate a significant tumor suppression by blocking PD-L1 in combination to NE-DHA-SBT-1214. Blockade of PD-L1 increased intratumoral IFN-gamma producing T cells and infiltration of inflammatory macrophages, which directly leads to the anti-tumor effect. In contrast, both PD-1 and PD-L1 level was high in combination of commonly used anti-cancer agents emphasizing increased tumor infiltration of Treg cells, which might be primarily responsible for the non-antitumor effect.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

1. Siegel R L, Miller K D, Jemal A. Cancer statistics, 2015. C A Cancer J Clin 2015; 65: 5-29.
2. Semenas J, Allegrucci C, Boorjian S A, Mongan N P, Persson J L. Overcoming drug resistance and treating advanced prostate cancer. Curr Drug Targets 2012; 13: 1308-23.
3. Ni J, Cozzi P, Hao J, Duan W, Graham P, Kearsley J, Li Y. Cancer stem cells in prostate cancer chemoresistance. Curr Cancer Drug Targets 2014; 14: 225-40.
4. Mazur P K, Siveke J T. Genetically engineered mouse models of pancreatic cancer: unravelling tumour biology and progressing translational oncology. Gut 2012; 61: 1488-500.

5. Dorado J, Lonardo E, Miranda-Lorenzo I, Heeschen C. Pancreatic cancer stem cells: new insights and perspectives. J Gastroenterol 2011; 46: 966-73.
6. Vredenburg M R, Ojima I, Veith J, Pera P, Kee K, Cabral F, Sharma A, Kanter P, Greco W R, Bernacki R J. Effects of orally active taxanes on P-glycoprotein modulation and colon and breast carcinoma drug resistance. Journal of the National Cancer Institute 2001; 93: 1234-45.
7. Von Hoff D D, Ervin T, Arena F P, Chiorean E G, Infante J, Moore M, Seay T, Tjulandin S A, Ma W W, Saleh M N, Harris M, Reni M, et al. Increased survival in pancreatic cancer with nab-paclitaxel plus gemcitabine. N Engl J Med 2013; 369: 1691-703.
8. Conroy T, Desseigne F, Ychou M, Bouche O, Guimbaud R, Becouarn Y, Adenis A, Raoul J L, Gourgou-Bourgade S, de la Fouchardiere C, Bennouna J, Bachet J B, et al. FOLFIRINOX versus gemcitabine for metastatic pancreatic cancer. N Engl J Med 2011; 364: 1817-25.
9. Hutchinson L, Kirk R. High drug attrition rates—where are we going wrong? Nature reviews Clinical oncology 2011; 8: 189-90.
10. Zhu L, Gibson P, Currle D S, Tong Y, Richardson R J, Bayazitov I T, Poppleton H, Zakharenko S, Ellison D W, Gilbertson R J. Prominin 1 marks intestinal stem cells that are susceptible to neoplastic transformation. Nature 2009; 457: 603-7.
11. Ojima I, Chen J, Sun L, Borella C P, Wang T, Miller M L, Lin S, Geng X, Kuznetsova L, Qu C, Gallager D, Zhao X, et al. Design, synthesis, and biological evaluation of new-generation taxoids. J Med Chem 2008; 51: 3203-21.
12. Botchkina G I, Zuniga E S, Das M, Wang Y, Wang H, Zhu S, Savitt A G, Rowehl R A, Leyfman Y, Ju J, Shroyer K, Ojima I. New-generation taxoid SB-T-1214 inhibits stem cell-related gene expression in 3D cancer spheroids induced by purified colon tumor-initiating cells. Molecular cancer 2010; 9: 192.
13. Das M, Zuniga E, Ojima I. Novel Taxoid-Based Tumor-Targeting Drug Conjugates. Chim Oggi 2009; 27: 54-6.
14. Sauer L A, Dauchy R T. The effect of omega-6 and omega-3 fatty acids on 3H-thymidine incorporation in hepatoma 7288CTC perfused in situ. British journal of cancer 1992; 66: 297-303.
15. Jones R J, Hawkins R E, Eatock M M, Ferry D R, Eskens F A, Wilke H, Evans T R. A phase II open-label study of DHA-paclitaxel (Taxoprexin) by 2-h intravenous infusion in previously untreated patients with locally advanced or metastatic gastric or oesophageal adenocarcinoma. Cancer Chemother Pharmacol 2008; 61: 435-41.
16. Harries M, O'Donnell A, Scurr M, Reade S, Cole C, Judson I, Greystoke A, Twelves C, Kaye S. Phase I/II study of DHA-paclitaxel in combination with carboplatin in patients with advanced malignant solid tumours. British journal of cancer 2004; 91: 1651-5.
17. Hennenfent K L, Govindan R. Novel formulations of taxanes: a review. Old wine in a new bottle? Ann Oncol 2006; 17: 735-49.
18. Kuznetsova L, Chen J, Sun L, Wu X, Pepe A, Veith J M, Pera P, Bernacki R J, Ojima 1. Syntheses and evaluation of novel fatty acid-second-generation taxoid conjugates as promising anticancer agents. Bioorganic & medicinal chemistry letters 2006; 16: 974-7.
19. Ahmad G, El Sadda R, Botchkina G, Ojima 1, Egan J, Amiji M. Nanoemulsion formulation of a novel taxoid DHA-SBT-1214 inhibits prostate cancer stem cell-induced tumor growth. Cancer letters 2017; 406: 71-80.
20. Couzin-Frankel J. Breakthrough of the year 2013. Cancer immunotherapy. Science 2013; 342: 1432-3.
21. Chen L. Co-inhibitory molecules of the B7-CD28 family in the control of T-cell immunity. Nature reviews Immunology 2004; 4: 336-47.
22. Brahmer J R, Hammers H, Lipson E J. Nivolumab: targeting PD-1 to bolster antitumor immunity. Future Oncol 2015; 11: 1307-26.
23. Brahmer J, Reckamp K L, Baas P, Crino L, Eberhardt W E, Poddubskaya E, Antonia S, Pluzanski A, Vokes E E, Holgado E, Waterhouse D, Ready N, et al. Nivolumab versus Docetaxel in Advanced Squamous-Cell Non-Small-Cell Lung Cancer. N Engl J Med 2015; 373: 123-35.
24. Larkin J, Hodi F S, Wolchok J D. Combined Nivolumab and Ipilimumab or Monotherapy in Untreated Melanoma. N Engl J Med 2015; 373: 1270-1.
25. Motzer R J, Rini B I, McDermott D F, Redman B G, Kuzel™, Harrison M R, Vaishampayan U N, Drabkin H A, George S, Logan T F, Margolin K A, Plimack E R, et al. Nivolumab for Metastatic Renal Cell Carcinoma: Results of a Randomized Phase II Trial. Journal of clinical oncology official journal of the American Society of Clinical Oncology 2015; 33: 1430-7.
26. Li X, Hu W, Zheng X, Zhang C, Du P, Zheng Z, Yang Y, Wu J, Ji M, Jiang J, Wu C. Emerging immune checkpoints for cancer therapy. Acta Oncol 2015; 54: 1706-13.
27. Jiang C, Cai X, Zhang H, Xia X, Zhang B, Xia L. Activity and Immune Correlates of a Programmed Death-1 Blockade Antibody in the treatment of Refractory Solid Tumors. J Cancer 2018; 9: 205-12.
28. Xu-Monette Z Y, Zhang M, Li J, Young K H. PD-1/PD-L1 Blockade: Have We Found the Key to Unleash the Antitumor Immune Response? Front Immunol 2017; 8: 1597.
29. Wang Y, Wu L, Tian C, Zhang Y. PD-1-PD-L1 immune-checkpoint blockade in malignant lymphomas. Ann Hematol 2017.
30. Torphy R J, Schulick R D, Zhu Y. Newly Emerging Immune Checkpoints: Promises for Future Cancer Therapy. Int J Mol Sci 2017; 18.
31. They L, Michaud H A, Becquart O, Lafont V, Guillot B, Boissiere-Michot F, Jarlier M, Mollevi C, Eliaou J F, Bonnefoy N, Gros L. PD-1 blockade at the time of tumor escape potentiates the immune-mediated antitumor effects of a melanoma-targeting monoclonal antibody. Oncoimmunology 2017; 6: e1353857.
32. Nomi T, Sho M, Akahori T, Hamada K, Kubo A, Kanehiro H, Nakamura S, Enomoto K, Yagita H, Azuma M, Nakajima Y. Clinical significance and therapeutic potential of the programmed death-1 ligand/programmed death-1 pathway in human pancreatic cancer. Clinical cancer research: an official journal of the American Association for Cancer Research 2007; 13: 2151-7.
33. Okudaira K, Hokari R, Tsuzuki Y, Okada Y, Komoto S, Watanabe C, Kurihara C, Kawaguchi A, Nagao S, Azuma M, Yagita H, Miura S. Blockade of B7-H1 or B7-DC induces an anti-tumor effect in a mouse pancreatic cancer model. Int J Oncol 2009; 35: 741-9.
34. Brahmer J R, Drake C G, Wollner I, Powderly J D, Picus J, Sharfman W H, Stankevich E, Pons A, Salay T M, McMiller T L, Gilson M M, Wang C, et al. Phase I study of single-agent anti-programmed death-1 (MDX-1106) in refractory solid tumors: safety, clinical activity, pharmacodynamics, and immunologic correlates. Journal of clinical oncology: official journal of the American Society of Clinical Oncology 2010; 28: 3167-75.
35. Brahmer J R, Tykodi S S, Chow L Q, Hwu W J, Topalian S L, Hwu P, Drake C G, Camacho L H, Kauh J, Odunsi K, Pitot H C, Hamid O, et al. Safety and activity of anti-PD-L1 antibody in patients with advanced cancer. N Engl J Med 2012; 366: 2455-65.
36. Le D T, Lutz E, Uram J N, Sugar E A, Onners B, Solt S, Zheng L, Diaz L A, Jr., Donehower R C, Jaffee E M, Laheru D A. Evaluation of ipilimumab in combination with allogeneic pancreatic tumor cells transfected with a G M-CSF gene in previously treated pancreatic cancer. J Immunother 2013; 36: 382-9.
37. Lutz E R, Wu A A, Bigelow E, Sharma R, Mo G, Soares K, Solt S, Dorman A, Wamwea A, Yager A, Laheru D, Wolfgang C L, et al. Immunotherapy converts nonimmunogenic pancreatic tumors into immunogenic foci of immune regulation. Cancer Immunol Res 2014; 2: 616-31.
38. Zhang P, Su D M, Liang M, Fu J. Chemopreventive agents induce programmed death-1-ligand 1 (P D-L1) surface expression in breast cancer cells and promote P D-L1-mediated T cell apoptosis. Mol Immunol 2008; 45: 1470-6.
39. Ghebeh H, Lehe C, Barhoush E, A I-Romaih K, Tulbah A, A I-Alwan M, Hendrayani S F, Manogaran P, Alaiya A, A I-Tweigeri T, Aboussekhra A, Dermime S. Doxorubicin downregulates cell surface B7-H1 expression and upregulates its nuclear expression in breast cancer cells: role of B7-H1 as an anti-apoptotic molecule. Breast cancer research: BCR 2010; 12: R48.
40. Gong W, Song Q, Lu X, Gong W, Zhao J, Min P, Yi X. Paclitaxel induced B7-H1 expression in cancer cells via the MAPK pathway. J Chemother 2011; 23: 295-9.
41. Peng J, Hamanishi J, Matsumura N, Abiko K, Murat K, Baba T, Yamaguchi K, Horikawa N, Hosoe Y, Murphy S K, Konishi I, Mandai M. Chemotherapy Induces Programmed Cell Death-Ligand 1 Overexpression via the Nuclear Factor-kappaB to Foster an Immunosuppressive Tumor Microenvironment in Ovarian Cancer. Cancer research 2015; 75: 5034-45.
42. Ojima I, Wang T, Miller M L, Lin S, Borella C P, Geng X, Pera P, Bernacki R J. Synthesis and structure-activity relationships of new second-generation taxoids. Bioorg Med Chem Lett 1999; 9: 3423-8.
43. Ojima I, Slater J C, Michaud E, Kuduk S D, Bounaud P Y, Vrignaud P, Bissery M C, Veith J M, Pera P, Bernacki R J. Syntheses and structure-activity relationships of the second-generation antitumor taxoids: exceptional activity against drug-resistant cancer cells. J Med Chem 1996; 39: 3889-96.
44. Shah L, Gattacceca F, Amiji M M. CNS delivery and pharmacokinetic evaluations of DALDA analgesic peptide analog administered in Nano-sized oil-in-water emulsion formulation. Pharmaceutical research 2014; 31: 1315-24.
45. Kadakia E, Shah L, Amiji M M. Mathematical Modeling and Experimental Validation of Nanoemulsion-Based Drug Transport across Cellular Barriers. Pharmaceutical research 2017; 34: 1416-27.
46. Ganta S, Singh A, Rawal Y, Cacaccio J, Patel N R, Kulkarni P, Ferris C F, Amiji M M, Coleman T P. Formulation development of a novel targeted theranostic nanoemulsion of docetaxel to overcome multidrug resistance in ovarian cancer. Drug Deliv 2016; 23: 968-80.
47. Morikane K, Tempero R M, Sivinski C L, Nomoto M, Van Lith M L, Muto T, Hollingsworth M A. Organ-specific pancreatic tumor growth properties and tumor immunity. Cancer Immunol Immunother 1999; 47: 287-96.
48. Sarker D K. Engineering of nanoemulsions for drug delivery. Current drug delivery 2005; 2: 297-310.
49. Maude S L, Frey N, Shaw P A, Aplenc R, Barrett D M, Bunin N J, Chew A, Gonzalez V E, Zheng Z, Lacey S F, Mahnke Y D, Melenhorst J J, et al. Chimeric antigen receptor T cells for sustained remissions in leukemia. N Engl J Med 2014; 371: 1507-17.
50. Rowinsky E K. The development and clinical utility of the taxane class of antimicrotubule chemotherapy agents. Annu Rev Med 1997; 48: 353-74.
51. McGuire W P, Rowinsky E K, Rosenshein N B, Grumbine F C, Ettinger D S, Armstrong D K, Donehower R C. Taxol: a unique antineoplastic agent with significant activity in advanced ovarian epithelial neoplasms. Ann Intern Med 1989; 111: 273-9.
52. Schiff P B, Horwitz S B. Taxol stabilizes microtubules in mouse fibroblast cells. Proc Natl Acad Sci USA 1980; 77: 1561-5.
53. Jordan M A, Toso R J, Thrower D, Wilson L. Mechanism of mitotic block and inhibition of cell proliferation by taxol at low concentrations. Proc Natl Acad Sci USA 1993; 90: 9552-6.
54. Maeda H, Wu J, Sawa T, Matsumura Y, Hori K. Tumor vascular permeability and the EPR effect in macromolecular therapeutics: a review. J Control Release 2000; 65: 271-84.
55. Rossi J, Giasson S, Khalid M N, Delmas P, Allen C, Leroux J C. Long-circulating poly(ethylene glycol)-coated emulsions to target solid tumors. Eur J Pharm Biopharm 2007; 67: 329-38.
56. Bocci G, Danesi R, Di Paolo A D, Innocenti F, Allegrini G, Falcone A, Melosi A, Battistoni M, Barsanti G, Conte P F, Del Tacca M. Comparative pharmacokinetic analysis of 5-fluorouracil and its major metabolite 5-fluoro-5,6-dihydrouracil after conventional and reduced test dose in cancer patients. Clinical cancer research: an official journal of the American Association for Cancer Research 2000; 6: 3032-7.
57. Kroep J R, Giaccone G, Voorn D A, Smit E F, Beijnen J H, Rosing H, van Moorsel C J, van Groeningen C J, Postmus P E, Pinedo H M, Peters G J. Gemcitabine and paclitaxel: pharmacokinetic and pharmacodynamic interactions in patients with non-small-cell lung cancer. Journal of clinical oncology: official journal of the American Society of Clinical Oncology 1999; 17: 2190-7.
58. Sakai H, Kokura S, Ishikawa T, Tsuchiya R, Okajima M, Matsuyama T, Adachi S, Katada K, Kamada K, Uchiyama K, Handa O, Takagi T, et al. Effects of anticancer agents on cell viability, proliferative activity and cytokine production of peripheral blood mononuclear cells. J Clin Biochem Nutr 2013; 52: 64-71.
59. Okino H, Maeyama R, Manabe T, Matsuda T, Tanaka M. Trans-tissue, sustained release of gemcitabine from photocured gelatin gel inhibits the growth of heterotopic human pancreatic tumor in nude mice. Clinical cancer research: an official journal of the American Association for Cancer Research 2003; 9: 5786-93.
60. Pardoll D M. The blockade of immune checkpoints in cancer immunotherapy. Nature reviews Cancer 2012; 12: 252-64.
61. Freeman G J, Long A J, Iwai Y, Bourque K, Chernova T, Nishimura H, Fitz L J, Malenkovich N, Okazaki T, Byrne M C, Horton H F, Fouser L, et al. Engagement of the PD-1 immunoinhibitory receptor by a novel B7 family member leads to negative regulation of lymphocyte activation. J Exp Med 2000; 192: 1027-34.

62. Latchman Y, Wood C R, Chernova T, Chaudhary D, Borde M, Chernova I, Iwai Y, Long A J, Brown J A, Nunes R, Greenfield E A, Bourque K, et al. P D-L2 is a second ligand for PD-1 and inhibits T cell activation. Nat Immunol 2001; 2: 261-8.
63. Nishimura H, Honjo T. PD-1: an inhibitory immunoreceptor involved in peripheral tolerance. Trends Immunol 2001; 22: 265-8.
64. Okazaki T, Maeda A, Nishimura H, Kurosaki T, Honjo T. PD-1 immunoreceptor inhibits B cell receptor-mediated signaling by recruiting src homology 2-domain-containing tyrosine phosphatase 2 to phosphotyrosine. Proc Natl Acad Sci USA 2001; 98: 13866-71.
65. Iwai Y, Terawaki S, Honjo T. PD-1 blockade inhibits hematogenous spread of poorly immunogenic tumor cells by enhanced recruitment of effector T cells. Int Immunol 2005; 17: 133-44.
66. Dong H, Strome S E, Salomao D R, Tamura H, Hirano F, Flies D B, Roche P C, Lu J, Zhu G, Tamada K, Lennon V A, Celis E, et al. Tumor-associated B7-H1 promotes T-cell apoptosis: a potential mechanism of immune evasion. Nature medicine 2002; 8: 793-800.
67. Hirano F, Kaneko K, Tamura H, Dong H, Wang S, Ichikawa M, Rietz C, Flies D B, Lau J S, Zhu G, Tamada K, Chen L. Blockade of B7-H1 and PD-1 by monoclonal antibodies potentiates cancer therapeutic immunity. Cancer research 2005; 65: 1089-96.
68. Lukens J R, Cruise M W, Lassen M G, Hahn Y S. Blockade of PD-1/B7-H1 interaction restores effector CD8+ T cell responses in a hepatitis C virus core murine model. J Immunol 2008; 180: 4875-84.
69. Guiducci C, Vicari A P, Sangaletti S, Trinchieri G, Colombo M P. Redirecting in vivo elicited tumor infiltrating macrophages and dendritic cells towards tumor rejection. Cancer research 2005; 65: 3437-46.

What is claimed is:

1. A pharmaceutical composition comprising an omega-3 polyunsaturated fatty acid (PUFA)-taxoid conjugate formulated in an oil-in-water nanoemulsion (NE) drug delivery system in combination with an immune-oncology (10) agent of anti-PD-L1 antibody, wherein said PUFA-taxoid conjugate is NE-DHA-SBT-1214.

2. The pharmaceutical composition of claim 1, wherein said PUFA is chosen from the group consisting of docosahexaenoic acid (DHA), eicosapentaenoic acid (EPA), and alpha-linolenic acid (LNA).

3. The pharmaceutical composition of claim 1, wherein said oil-in-water NE includes omega-3 fatty acid-rich edible oil.

4. The pharmaceutical composition of claim 3, wherein said omega-3 fatty acid-rich edible oil is chosen from the group consisting of fish oil, flax-seed oil, pine nut oil, safflower oil, primrose oil, black currant oil, borage oil, wheat germ oil, chia oil, hemp oil, perilla oil, grape oil, squalene oil, and fungal oil.

5. The pharmaceutical composition of claim 3, wherein said omega-3 fatty acid-rich edible oil is modified with a compound chosen from the group consisting of surfactants and targeting agents.

6. A method of treating cancer, including the steps of:
administering an effective amount of a pharmaceutical composition including a PUFA-taxoid conjugate encapsulated in an NE drug delivery system, wherein said PUFA-taxoid conjugate is NE-DHA-SBT-1214, in combination with an IO agent of to a subject in need of treatment; and
treating pancreatic cancer.

7. The method of claim 6, further including the steps of increasing expression of PD-L1 in the tumor microenvironment, increasing $CD4^+$ and $CD8^+$ tumor-infiltrating lymphocytes, and making the subject more responsive to the IO agent.

8. The method of claim 6, wherein the cancer is highly drug resistant.

9. The method of claim 6, further including the step of down-regulating survival genes in tumors and activating p53 and p21.

10. The method of claim 6, wherein the PUFA is chosen from the group consisting of docosahexaenoic acid (DHA), eicosapentaenoic acid (EPA), and alpha-linolenic acid (LNA).

11. The method of claim 6, further including the step of upregulating PD-L1.

12. The method of claim 6, wherein the oil-in-water NE includes omega-3 fatty acid-rich edible oil.

13. The method of claim 12, wherein the omega-3 fatty acid-rich edible oil is chosen from the group consisting of fish oil, flax-seed oil, pine nut oil, safflower oil, primrose oil, blackcurrant oil, borage oil, wheat germ oil, chia oil, hemp oil, perilla oil, grape oil, squalene oil, and fungal oil.

14. The method of claim 12, wherein the omega-3 fatty acid-rich edible oil is modified with a compound chosen from the group consisting of surfactants and targeting agents.

15. The method of claim 6, wherein a tumor treated has less dense stroma after treatment.

16. The method of claim 6, further including the steps of increasing intra-tumoral IFN-gamma producing T cells and inducing infiltration of inflammatory macrophages.

* * * * *